United States Patent [19]

Smith et al.

[11] Patent Number: 5,751,415
[45] Date of Patent: May 12, 1998

[54] RAMAN SPECTROSCOPY APPARATUS AND METHOD FOR CONTINUOUS CHEMICAL ANALYSIS OF FLUID STREAMS

[75] Inventors: Lee M. Smith, Salt Lake City; Robert E. Benner, Holladay; Douglas A. Christensen; Joel M. Harris, both of Salt Lake City; Carl W. Johnson, Midvale; Richard D. Rallison, Paradise, all of Utah

[73] Assignee: Process Instruments, Inc., Salt Lake City, Utah

[21] Appl. No.: 647,586

[22] Filed: May 13, 1996

[51] Int. Cl.⁶ .................................................... G01J 3/44
[52] U.S. Cl. ........................................ 356/301; 356/328
[58] Field of Search ................... 356/70, 301, 317–318, 356/300, 334, 410, 328, 440, 417, 436, 73, 326; 250/227.23, 573, 574

[56] References Cited

U.S. PATENT DOCUMENTS

| | | |
|---|---|---|
| 3,906,241 | 9/1975 | Thompson . |
| 4,416,505 | 11/1983 | Dickson . |
| 4,530,564 | 7/1985 | Close . |
| 4,540,280 | 9/1985 | Anderson et al. . |
| 4,573,761 | 3/1986 | Mclachlan et al. . |
| 4,579,457 | 4/1986 | Guigues . |
| 4,630,923 | 12/1986 | Tans et al. . |
| 4,783,168 | 11/1988 | Florisson et al. . |
| 4,786,171 | 11/1988 | LeFebre et al. . |
| 4,867,559 | 9/1989 | Bach . |
| 4,884,276 | 11/1989 | Dixon et al. . |
| 4,917,491 | 4/1990 | Ring et al. ................ 356/300 |
| 4,963,745 | 10/1990 | Maggard . |
| 4,973,561 | 11/1990 | Hansen et al. . |
| 4,995,050 | 2/1991 | Waarts et al. . |
| 5,011,284 | 4/1991 | Tedesco et al. . |
| 5,077,481 | 12/1991 | Hoult . |
| 5,112,127 | 5/1992 | Carrabba et al. . |
| 5,124,815 | 6/1992 | Chang . |
| 5,139,334 | 8/1992 | Clarke . |
| 5,166,747 | 11/1992 | Schroeder et al. . |
| 5,170,056 | 12/1992 | Berard et al. . |

(List continued on next page.)

FOREIGN PATENT DOCUMENTS

| | | |
|---|---|---|
| 228 990 | 10/1985 | Germany . |
| 56-55842 | 5/1981 | Japan . |
| 1-287448 | 1/1989 | Japan . |

OTHER PUBLICATIONS

Gilmore et al; Quantitative Detection of Environmentally Important Dyes ... Spectroscopy Applied Spectroscopy, vol. 49, Nov. 4, 1995, pp. 508–512.

(List continued on next page.)

*Primary Examiner*—K. Hantis
*Attorney, Agent, or Firm*—Madson & Metcalf

[57] ABSTRACT

Apparatus and methods for analyzing the chemical composition of fluid streams using Raman spectroscopy are disclosed. The invention is particularly useful in continuously analyzing a fluid stream containing petroleum products, aqueous or biological fluids. The apparatus includes a laser source for producing light having an excitation wavelength. The light is introduced into a bundle of optical fibers connected to a tubular Raman enhancement cell. A transparent optical element (lens and/or window) acts as a barrier element to isolate the flowing sample stream from the optical components. The Raman enhancement cell is configured to allow continuous sample fluid flow therethrough, and it is preferably lined with a material having an index of refraction less than the index of refraction of the fluid stream. Scattered light from the enhancement cell preferably exits the optical fibers as a linear optical signal. A Raman spectrometer passes the optical signal through an excitation wavelength filter, an optical slit, and a volume holographic transmission grating with an aberration correction device before transmitting the optical signal to a charge coupled device array which converts the optical signal into a corresponding electronic signal. The electronic signal is analyzed and converted by computer into a representation of the chemical analysis of the fluid stream.

45 Claims, 19 Drawing Sheets

U.S. PATENT DOCUMENTS

| | | |
|---|---|---|
| 5,194,910 | 3/1993 | Kirkpatrick, Jr. et al. |
| 5,220,401 | 6/1993 | Milsevic et al. |
| 5,225,679 | 7/1993 | Clarke et al. |
| 5,348,645 | 9/1994 | Maggard et al. |
| 5,349,188 | 9/1994 | Maggard . |
| 5,349,189 | 9/1994 | Maggard . |
| 5,360,972 | 11/1994 | DeFoggio et al. |
| 5,362,965 | 11/1994 | Maggard . |
| 5,377,004 | 12/1994 | Owen et al. |
| 5,381,237 | 1/1995 | Sela . |
| 5,402,241 | 3/1995 | Jeannotte et al. |
| 5,404,218 | 4/1995 | Nave et al. |
| 5,596,196 | 1/1997 | Cooper et al. |

OTHER PUBLICATIONS

J. B. Coopert et al., "Remote Fiber–Optic Raman Analysis of Xylene Isomers in Mock Petroleum Fuels Using a Low–Cost Dispersive Instrument and Partial Least–Squares Regression Analysis." *Applied Spectroscopy*, vol. 49, No. 5 (1995).

S. Michael Angel, Thomas M. Vess, and Michael L. Myrick. "Simultaneous Multi–Point Fiber–Optic Raman Sampling for Chemical Process Control Using Diode Lasers and CCDDetector." *SPIE Chemical, Biochemical, and Environmental Fiber Sensors III*, vol. 1587 (1991) pp. 219–231.

M. B. Seasholtz, D. D. Archibald, A. Lorber, and B. R. Kowalski, "Quantitative Analysis of Liquid Fuel Mixtures with the Use of Fourier Transform Near–IR Raman Spectroscopy." *Applied Spectroscopy*, vol. 43, No. 6 (1989) pp. 1067–1072.

K. P. J. Williams et al., "Determination of Gas Oil Cetane Number and Cetane Index Using Near Infrared Fourier Transform Raman Spectroscopy." *Anal. Chem.* (1990) 62 pp. 2553–2556.

M. D. Weiss, "NMR and Raman Spectroscopies Move from Lab to Plant." *Today's Chemist at Work* (Jan. 1995) pp. 25–28.

C. D. Newman et al., "Fiber–Optic Sampling Combined with an Imaging Spectrograph for Routine Raman Spectroscopy." *Applied Spectroscopy*, vol. 46, No. 2 (1992) pp. 262–265.

C. J. deBakker et al., "Determination of Petroleum Properties by Fiber–Optic Fourier Transform Raman Spectrometry and Partial Least—Squares Analysis." *Applied Spectroscopy*, vol. 49, No. 12 (1995).

J. B. Cooper et al., "Determination of Octane Numbers and Reid Vapor Pressure of Commercial Petroleum Fuels Using FT–Raman Spectroscopy and Partial Least—Squares Regression Analysis." *Analytical Chemistry*, vol. 67, No. 22 (Nov. 15, 1995) pp. 4096–4100.

W. R. Kalsi, A. S. Sarpal, S. K. Jain, S. P. Srivastava, and A. K. Bhatnagar, Determination of Oxygenates in Gasoline by $^1$H Nuclear Magnetic . . . . *Energy & Fuels*, pp. 574–579 May 4, 1995.

Andrew J. Vreugdenhil and Ian S. Butler, Detection of the Engine Anti–knock Additive Methylcyclopentadienyl Manganese Tricarbonyl (MMT) from . . . . *Applied Spectroscopy*, pp. 482–485 (1995).

Hillary L. MacDonald, Hao Liu, and Paul Yager, Fiber Optic Sensor for General Anesthetics based on Raman Spectroscopy, *SPIE*, pp. 514–524 (1994).

*Official Gazette* publication of Patent No. 5,363,463, p. 1302 Nov. 8, 1994.

Francisco X. Garcia, Lola de Lima, and Julio C. Medina, Determination of Methanol and Methyl tert–Butyl Ether in Gasoline by by . . . , *Applied Spectroscopy*, pp. 1036–1039 (1993).

Máximo Gallignani, Salvador Garrigues, and Miguel de la Guardia, Direct Determination of Benzene in Gasoline by Flow–Injection Injection Fourier Transform Infrared . . . , pp. 267–274, (1993).

*Official Gazette* publication of Patent No. 5,112,127, p. 912 May 12, 1992.

Chen Zhaohui and Feng Xinlu, Use NIR Spectroscopy for On–Line Gasoline Analysis, *Hydrocarbon Processing*, pp. 94–96 (Jan. 1992).

Yan Wang and Richard L. McCreery, Evaluation of a Diode Laser/Charge Coupled Device Spectrometer for Near–Infrared Raman Spectroscopy, *Analytical Chemistry*, vol. 61 No. 23, pp. 2647–2651 Dec. 1, 1989.

*Official Gazette* publication of Patent No. 4,858,238, p. 2092 Aug. 15, 1989.

*Official Gazette* publication of Patent No. 4,645,340 Feb. 24, 1987.

Scott D. Schwab and Richard L. McCreery, Remote, Long–Pathlength Cell for High–Sensitivity Raman Spectroscopy, *Applied Spectroscopy* vol. 41, No. 1, pp. 126–130 (1987).

*Official Gazette* publication of Patent No. 4,630,923, p. 2022 (23/23/86).

RAMAN SPECTROSCOPY APPARATUS AND METHOD FOR CONTINUOUS CHEMICAL ANALYSIS OF FLUID STREAMS

GOVERNMENT RIGHTS

This invention was made with Government support under SBIR contracts No. F29601-96-C-0029 and No. F29601-96-C-0048 awarded by The Department of Defense, and National Science Foundation STTR Grant No. DMI-9522728.

FIELD OF THE INVENTION

The present invention is directed to an apparatus and method for continuous chemical analysis of fluid streams, particularly fluid streams containing petroleum products, using Raman spectroscopy. The technique can also be applied equally well to aqueous streams and biological samples.

TECHNOLOGY BACKGROUND

The refining and processing of crude petroleum into commercially useful petroleum products is a vital industry around the world. One of the most important petroleum products is the class of gasoline fuels. Gasoline fuels consist of a mixture of various hydrocarbon compounds. The concentration and chemical grouping of these hydrocarbon compounds determines the resulting fuel properties such as octane number and Reid vapor pressure (RVP).

Reid vapor pressure provides a volatility measurement of the gasoline. The octane number for a gasoline fuel is defined in terms of its knocking characteristics relative to a standard blend of isooctane (2,3,4-trimethylpentane) and n-heptane. Arbitrarily, an octane number of zero has been assigned to n-heptane and a rating of 100 to isooctane. Thus, an unknown fuel having a knocking tendency equal to a blend of 90% isooctane and 10% n-heptane, by volume, is assigned an octane number of 90.

During the manufacture of various grades of gasoline, it is useful to monitor the final product to be sure it possesses the desired physical properties, such as octane number. However, there currently is not a quick and inexpensive system for continuously monitoring a gasoline fuel composition. Instead periodic samples are normally taken from the process stream and analyzed. Occasionally, a gasoline fuel blend sold at one octane rating actually has a higher octane rating. This is uneconomical, since higher octane gasolines are more valuable to the refinery than lower octane gasolines.

It is also useful to control the concentration of various hydrocarbon ingredients in the gasoline blend. For instance, it is desirable to reduce the concentration of benzene, a known carcinogen, in gasoline. Yet, benzene concentration is often difficult to measure using conventional analysis. It is also desirable to minimize the olefin concentration. Olefins are unsaturated hydrocarbons (containing C=C bonds) which are photoreactive and contribute to smog formation. Olefins are also hard to measure accurately using conventional techniques. Finally, because xylene is a valuable gasoline ingredient, excess xylene should be minimized. It also would be valuable to identify and quantify the xylene isomers (para, meta, and ortho) present in the gasoline, but conventional analytical techniques cannot quickly distinguish between the xylene isomers. Thus, it would be a significant advancement in the art to permit continuous monitoring of the gasoline's chemical composition and physical properties.

Concentrated sulfuric acid is used by refineries in the alkylation process. The sulfuric acid concentration needs to be carefully controlled between 90% and 98% during the alkylation process. Currently, refineries manually take individual "grab-samples." Because of the unreacted hydrocarbon contamination in the acid, the samples require centrifuging to separate the acid. The acid is then titrated in the laboratory to determine exact acid content. These tests are typically run every four hours. Because of the time constraints with this type of testing, the refineries tend to run much higher acid concentrations than they would like to ensure that the process proceeds uninterrupted. Maintaining an excessively high acid concentration costs millions of dollars annually at each refinery.

When the acid concentration reaches 89%, it is removed from the process and hauled back to a chemical plant for recycling. This process of constantly removing, adding and transporting concentrated sulfuric acid is expensive and potentially dangerous. Because of the high cost of sulfuric acid, Amoco Oil Company calculates that for each 0.5% drop in average acid content in their alkylation process, they could save $5,000,000 per year throughout their entire production system. It is estimated that a continuous, on-line, analysis of acid concentration would enable the average acid concentration to be reduced by about 1%. Taking into account the additional savings from reduced transportation and handling costs, this total savings could average $12,000,000 per year for Amoco Oil. The sulfuric acid concentration problem is universal for the petroleum industry, and it has been estimated that a continuous, on-line chemical stream analysis could save the U.S. petroleum industry over $100,000,000 annually, with some of this savings returning to customers.

The alkylation process does not react the same with all alkene compounds; propylene compounds for instance, react much differently than do most other alkenes. The alkylation process needs a rapid, on-line control to properly react to changing feed stocks, to efficiently adjust acid levels, and economically produce petroleum products from a wide variety of incoming crude oil. Thus, there is a significant need in the art for a process and method which allows on-line analysis and control of acid content of such process streams.

Raman spectroscopy is an analytical technique which uses light scattering to identify and quantify molecules. When light of a single wavelength (monochromatic) interacts with a molecule, the light scattered by the molecule contains small amounts of light with wavelengths different from the incident light. The wavelengths present in the scattered light are characteristic of the structure of the molecule, and the intensity of this light is dependent on the concentration of these molecules. Thus, the identities and concentrations of various molecules in a substance can be determined by illuminating the substance with monochromatic light and then measuring the individual wavelengths and their intensities in the scattered light.

A continuing problem with Raman spectroscopy is the very low intensity of the scattered light compared to the incident light. Elaborate spectrometers, having high light gathering power and dispersion, high stray light rejection, and sensitive detectors, are required to isolate and measure the low intensity Raman scattered light. These instruments are costly and delicate, and are not well suited for use in industrial manufacturing or processing facilities. As a result, they have rarely been used outside of laboratory environments. Improvements in the fields of lasers, optical fibers, and filters enable one to remotely locate a fiber-optic probe from its laser light source and from its spectrometer.

It will be appreciated that there is a need in the art for an apparatus and method for analyzing industrial fluid streams, particularly those containing petroleum products, which provides quick and accurate results.

SUMMARY OF THE INVENTION

The present invention is directed to an apparatus and method for analyzing the composition of a fluid stream using Raman spectroscopy. The invention is particularly useful in continuously analyzing a fluid stream containing petroleum products, such as gasoline fuel.

The apparatus includes a laser source for producing light having an excitation wavelength. Conventional laser diodes can be used as the light source. The light is introduced into a bundle of optical fibers containing an excitation optical fiber and a plurality of peripheral collection optical fibers. The fiber bundle is optically connected to a tubular Raman enhancement cell. The tubular Raman enhancement cell is configured to allow continuous sample fluid flow therethrough.

Light from the excitation optical fiber is coupled into the enhancement cell, and backscattered Raman signal (light) from the enhancement cell is coupled into the plurality of collection optical fibers. The optical fiber bundle is preferably separated from the flowing fluid sample within the enhancement cell by a transparent fluid barrier (an optical window and\or lens assembly).

The tubular Raman enhancement cell is preferably lined with a material having an index of refraction less than the index of refraction of the fluid stream so that light reflects internally at the interface between the fluid sample and the enhancement cell liner. This eliminates light losses which would otherwise occur if the light passed through the liner and was reflected at the exterior (air interface) surface of the liner.

Scattered light from the enhancement cell enters the plurality of collection fibers for transmission to a Raman spectrometer. The exit end of the collection fibers is preferably aligned in a linear array so that a linear optical signal is generated. The Raman spectrometer passes the linear optical signal through a filter to eliminate portions of the optical signal having the excitation wavelength. The linear optical signal is also passed through an optional optical slit. The optical slit typically has dimensions comparable to the linear array of collection optical fibers. The linear array of optical fibers can perform the same function as the optical slit by generating a linear optical signal. A commercially available charge coupled device converts the optical signal into a corresponding electronic signal to be analyzed by a computer and converted into a representation of the chemical analysis of the fluid stream.

A plurality of optical lenses are preferably provided to receive and convey the optical signal from the linear input array, through the Raman spectrometer, to the charge coupled device. A volume holographic transmission grating is used to disperse the signal, and an aberration correction element is provided to correct optical aberrations introduced into the optical signal by the volume holographic grating element. A pair of 45 degree, right angle prisms is one presently preferred aberration correction element. Other optically transparent components such as wedges can be used for aberration correction. If necessary, the focusing function of the optical lenses can be performed with the holographic grating.

The use of an aberration correction element in combination with a volume holographic transmission grating can be used in conventional Raman spectrometers without an enhancement cell or optical fibers. In such cases, solid or non-fluid samples can be analyzed using conventional techniques.

Through use of the optical fiber bundle, it is possible to locate the Raman enhancement cell in a remote location near an industrial process stream. The Raman spectrometer, laser source, and computer can be located in a distant, protected environment. The apparatus and method for analyzing the composition of a fluid stream using Raman spectroscopy is rapid and accurate. It has been shown to provide excellent analysis of fluid streams containing petroleum products. Of course, those skilled in the art will appreciate that the present invention can be readily adapted for use in analyzing other fluid streams such as aqueous streams and biological samples.

DETAILED DESCRIPTION OF THE PREFERRED EMBODIMENTS

Figure 1:
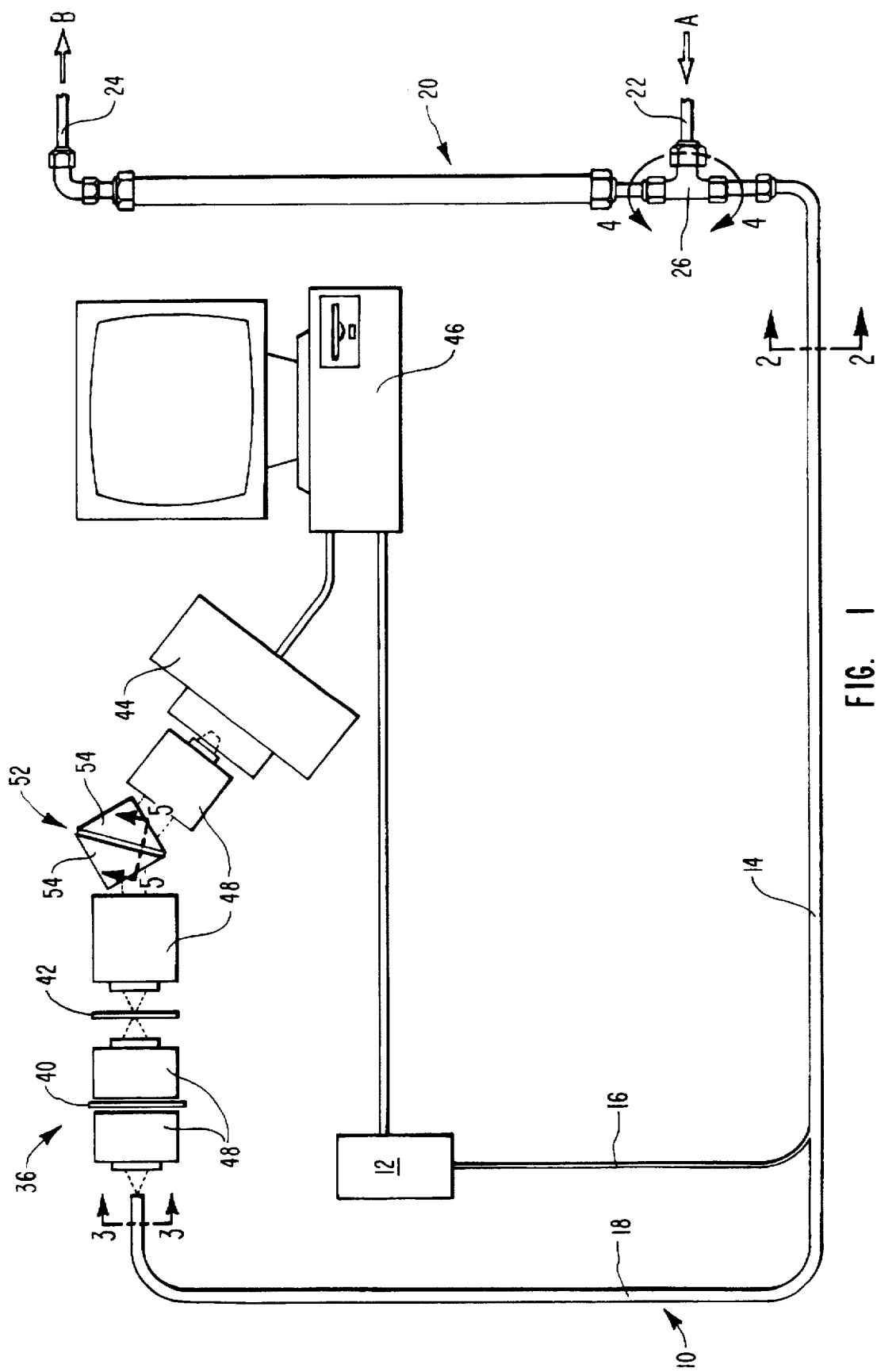
FIG. 1 is a schematic view of an apparatus for analyzing the composition of a fluid stream using Raman spectroscopy within the scope of the present invention.

Reference is now made to the figures wherein like parts are referred to by like numerals throughout. With particular reference to FIG. 1, a schematic representation of an apparatus 10 for analyzing the composition of a fluid stream using Raman spectroscopy is illustrated.

The apparatus includes a laser source 12 for producing light having an excitation wavelength. Conventional laser diodes can be used as the light source. Typical output power of the laser source can vary from 25 mW to 150 mW. The excitation wavelength is preferably in the range from 780 nm to 850 nm for use in Raman spectroscopy. Two suitable commercially available laser diodes are manufactured by Spectra Diode Labs, Inc., San Jose, Calif. and designated SDL-5402-H1 having a power of 50 mW at a wavelength of 785 nm and SDL-5412-H1 having a power of 100 mW at 802 nm.

Figure 2:
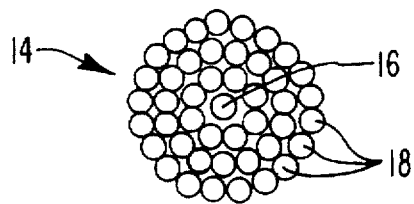
FIG. 2 is a cross sectional view of a bundle of optical fibers used to transmit light having an excitation wavelength and to receive scattered light.

The light is introduced into a bundle of optical fibers 14 containing a center, excitation optical fiber 16 and a plurality of peripheral collection optical fibers 18. One currently preferred optical fiber bundle 14 configuration is illustrated in FIG. 2. Such optical fiber bundles are commercially available from manufacturers such as Fiberguide Industries, Inc., Stirling, N.J. The fiber bundles preferably contain at least 30 or more fibers, and more preferably from 40 to 50 fibers. The individual fibers have a small size to maintain good spectral resolution. Optical fibers having a diameter in the range from about 50 microns to 100 microns are suitable, with the presently preferred size being about 100 microns. Typically, only one fiber is required as the excitation optical fiber, although it is possible to use more that one fiber to carry the excitation light. The remaining optical fibers are collection optical fibers to receive backscattered Raman signal (light).

The fiber bundle is optically connected to a tubular Raman enhancement cell 20. The Raman enhancement cell 20 is configured to allow continuous fluid flow therethrough, illustrated by arrows A and B. A fluid stream inlet 22 and a fluid stream outlet 24 are located adjacent the ends of the enhancement cell 20 to allow fluid flow through the enhancement cell 20. Experimental tests indicate that the fluid flow rate does not affect the Raman spectroscopy results and fluid flow can go in either direction. An optical connector 26 located at one end of the enhancement cell permits connection of the optical fiber bundle 14 to the enhancement cell 20.

Figure 4:
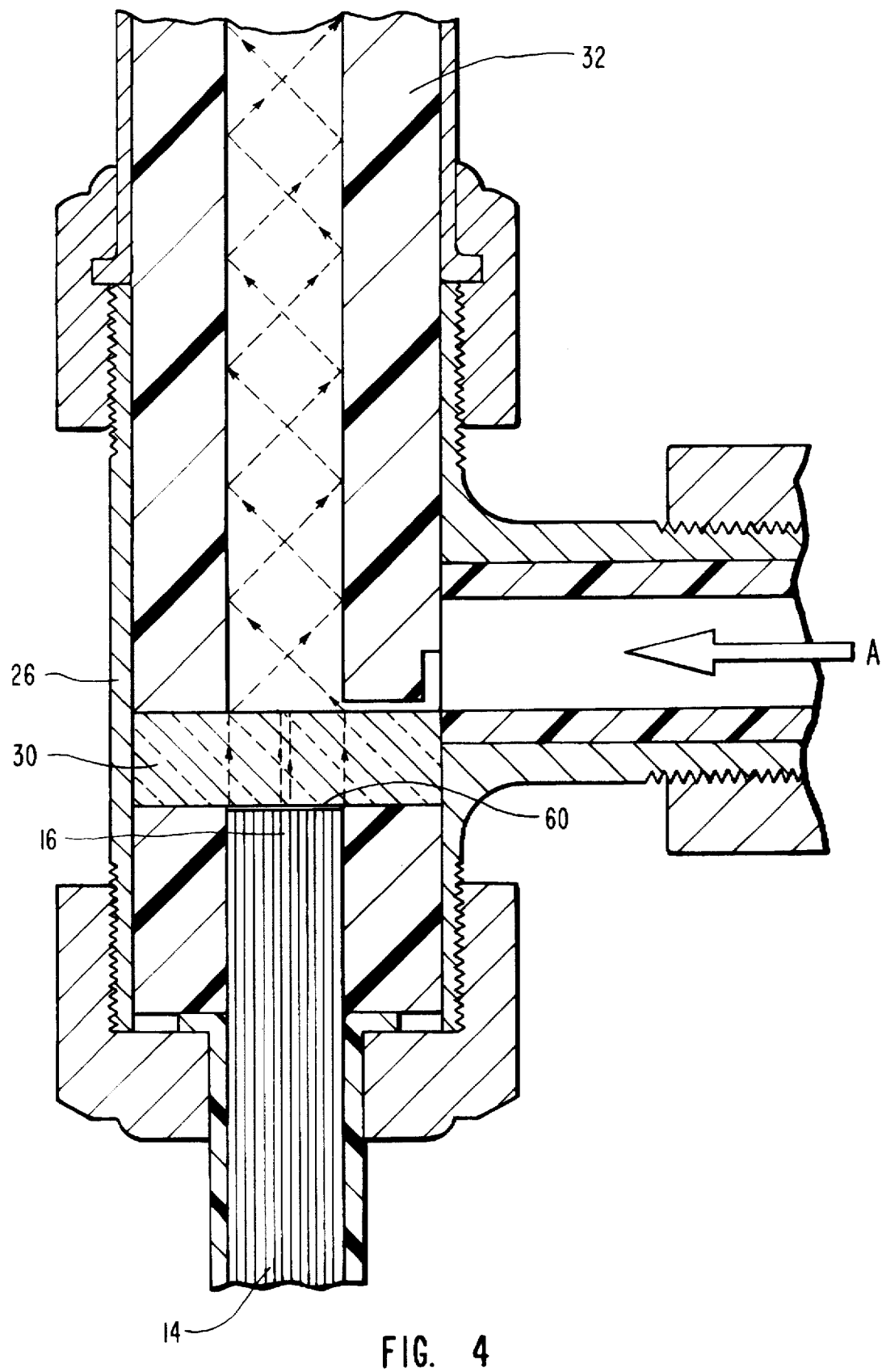
FIG. 4 is an enlarged cross sectional view of one end of a Raman enhancement cell showing connection of an optical fiber bundle and fluid entrance into the enhancement cell.

As shown best in FIG. 4, the Raman enhancement cell 20 preferably includes the close coupling of the adjacent bundle of optical fibers 14 to couple the light from the excitation optical fiber 16 into the enhancement cell 20 and to allow backscattered Raman light from the enhancement cell to enter the plurality of collection optical fibers. A transparent fluid barrier 30 is preferably located between the bundle of optical fibers 14 and the fluid flow (shown by arrow A) within the enhancement cell 20. An index matching fluid 60 is put between the fiber bundle tip and the barrier to improve optical coupling efficiency. Suitable index matching fluids are commercially available. They are typically clear viscous fluids, such as mineral oil or glycerol, which fill any voids between two optical surfaces. Optical epoxy can also be used, but it would result in permanent attachment of the fiber bundle to the fluid barrier.

The tubular Raman enhancement cell 20 is preferably lined with a waveguide core (liner) 32 having an index of refraction less than the index of refraction of the fluid stream. If the index of refraction of the liner is low enough, much of the light will reflect internally at the interface between the fluid sample and the enhancement cell liner 32, as shown in FIG. 4. Of course, the enhancement cell can be lined with a transparent material, such as glass, which will cause reflection to occur at the exterior surface of the liner. Because light loses some of its intensity as it passes through the liner, it is presently preferred to line the enhancement cell with a low index of refraction material. Fluorinated polymers, such as polytetrafluoroethylene (PTFE), PFA, copolymer of tetrafluoroethylene and hexafluoropropylene (FEP), AF and Tefzel, are currently preferred because they have indexes of refraction from below about 1.29 to 1.35. Preferred index of refraction is one that is less than the fluid being analyzed. The enhancement factor for the cell is dependent upon the refractive index of the sample solution in the cell. Different solution refractive indices result in different critical angles and different effective sample path lengths.

The length and width of the tubular Raman enhancement cell 20 can vary. Generally, a longer enhancement cell will yield a larger enhancement effect up to the point where additional cell length will have less and less effect because of internal losses in the liquid medium and the waveguide core. The tubular Raman enhancement cell 20 preferably has a length in the range from about 0.1 m to about 4 m, with a preferred length ranging from 1 to 2 meter, depending upon the degree of sensitivity desired. An enhancement cell length of one to two meters yields excellent amplification of the Raman signal while still being easy to fabricate and install.

The enhancement cell preferably has a diameter in the range from about 0.005 to 0.2 inches. For any given cell length, the smaller the waveguide diameter, the greater the enhancement effect. The preferred diameter is determined more by what size waveguide is the easiest to fabricate and produce and to what extent the Raman signal needs to be enhanced. A presently preferred diameter is about 0.03 inches, mainly because of the ease of fabrication and the ability to maintain a reasonable level of flow. Too small a diameter, such as 0.005 inches, will yield excellent Raman signal enhancement, but the pressure required to obtain a reasonable flow through the cell will be high. Too large of a diameter, i.e., greater than 0.2 inches, will greatly reduce the Raman signal enhancement effect for a practical length of waveguide.

Figure 22:
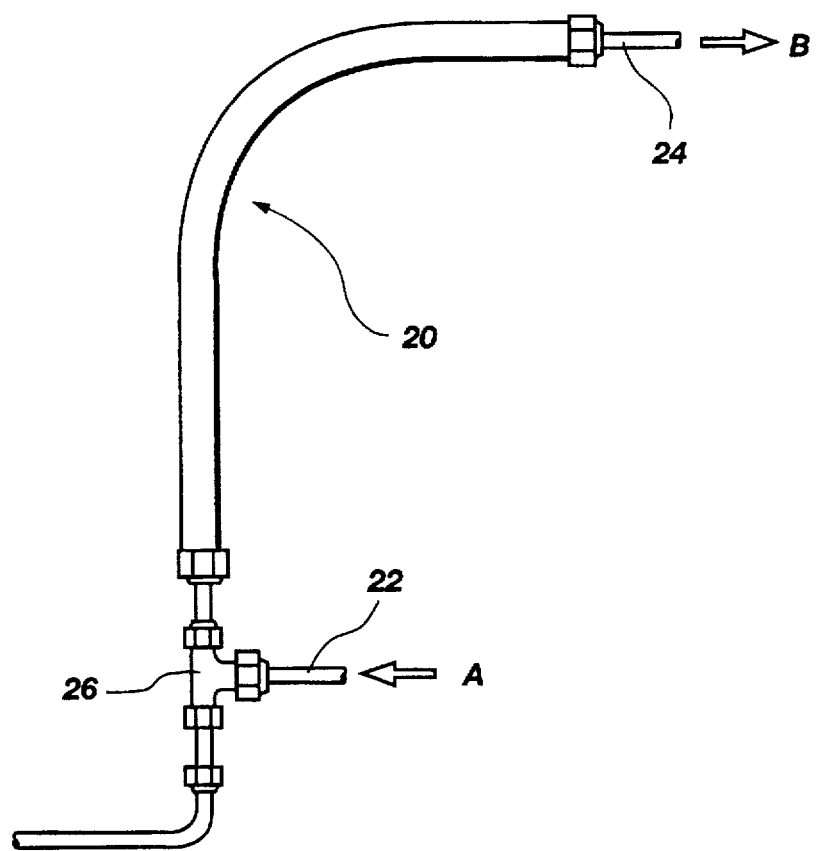
FIG. 22 is a schematic view of a Raman enhancement cell in a curved orientation between the fluid stream inlet and the fluid stream outlet.

The tubular Raman enhancement cell 20 may be rigid or flexible. In operation, acceptable performance is obtained with the enhancement cell in either linear, curved or coiled configurations. If the enhancement cell is coiled, it is preferred to maintain the bend radius greater than ½ inch to minimize signal loss caused by bending the waveguide. FIG. 22 shows the enhancement cell in one possible curved orientation.

Figure 3:
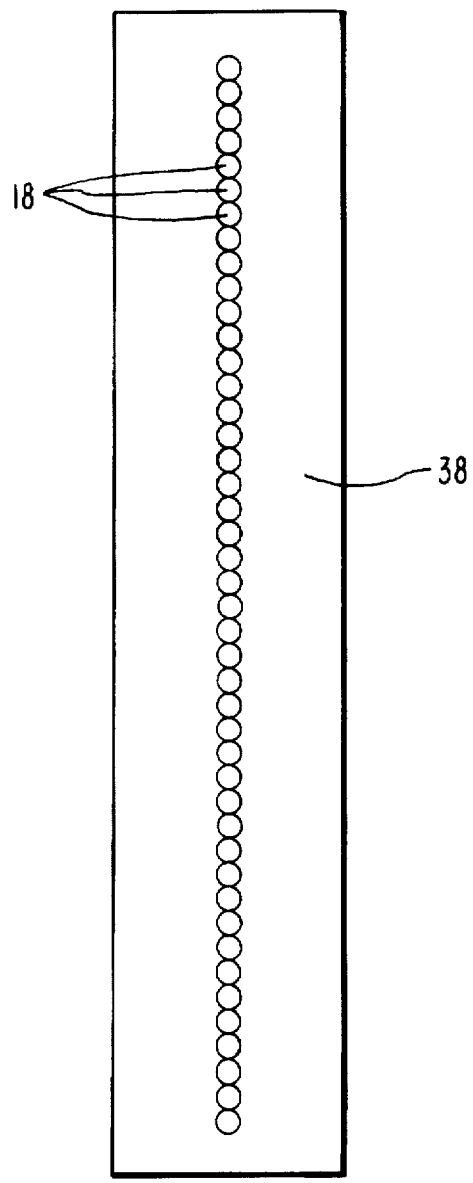
FIG. 3 is a cross sectional view of the linear array of collection optical fibers.

In use, scattered light from the enhancement cell enters the plurality of collection fibers for transmission to a Raman spectrometer 36. As shown in FIG. 3, the exit end of the collection fibers is preferably aligned in a linear array 38 so that a linear optical signal is generated. The Raman spectrometer 36 passes the linear optical signal through a filter 40 to eliminate portions of the optical signal having the excitation wavelength. A suitable filter must have good laser line rejection, such as a holographic or dielectric filter. Suitable dielectric filters are manufactured by optical filter companies such as Omega Optical. The holographic filter is made by companies such as Kaiser Optical, Ann Arbor, Mich. and Ralcon Development, Paradise, Utah.

The linear optical signal is also passed through an optical slit 42 to remove stray light. The optical slit 42 typically has dimensions comparable to the width and height of the linear array 38 of collection optical fibers. The narrower the slit the better the spectral resolution. However, this increased resolution also reduces the overall signal throughput. The optical slit preferably has a width in the range from 10 microns to 150 microns. In a currently preferred embodiment, the slit ranges from 7 mm×25 µm to 7 mm×100 µm. The linear array of optical fibers can perform the same function as the optical slit by generating a linear optical signal. In this manner, the slit and associated optics can be replaced by the linear array of optical fibers.

A commercially available charge coupled device ("CCD") 44 converts the optical signal into a corresponding electronic signal to be analyzed by a computer 46 and converted into a representation of the chemical analysis of the fluid stream. The computer 46 can also be used to control the laser source 12.

A plurality of optical lenses 48 are provided to receive and convey the optical signal from the linear array 38, through the Raman spectrometer 36, to the charge coupled device 44. The speed of the optical lenses can vary, but faster speeds are generally preferred in order to capture more light. The improved performance obtained by faster lenses must be balanced by the increased cost of the lenses. Optical lenses having a speed in the range from f/1.0 to f/2.8 have been found to be suitable.

Figure 5:
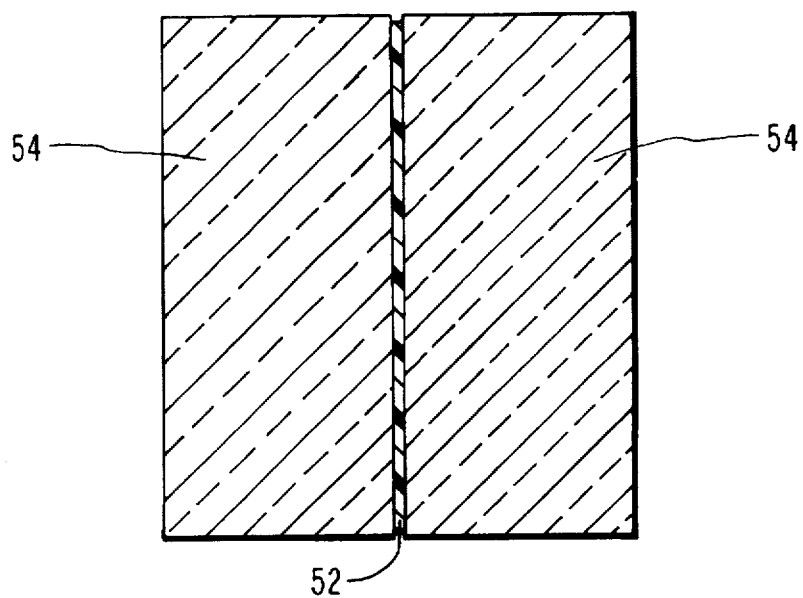
FIG. 5 is a cross sectional view of an aberration correction element and volume holographic grating within the scope of the present invention.

A volume holographic transmission grating 52 is used to disperse the signal. If necessary, the focusing function of the optical lenses can be performed with the volume holographic grating. An aberration correction element 54 is preferably provided to correct optical aberrations introduced into the optical signal by the volume holographic grating 52. One presently preferred aberration correction element 54, illustrated in FIG. 5, is a pair of 45° right-angle prisms 54. Other optically transparent components such as wedges can be used for aberration correction. The aberration correction elements could be joined together and placed in front of or behind the holographic grating element. It is important that the aberration correction element contain a sufficient thickness of optically transparent material to correct the aberrations produced by the volume holographic transmission grating.

The configuration shown in FIGS. 1 and 5 is currently preferred because it requires less space and allows the closer coupling of the optical elements, i.e. the grating, lenses, and CCD array. It also allows for the use of higher resolution gratings. The closer coupling allows for greater light throughput for any given lens size.

The volume holographic transmission grating 52 can be fabricated with various degrees of spectral resolution with equivalent grooves/mm from several hundred grooves/mm up to 2400 grooves/mm. The preferred resolution is on the order of 1500 grooves/mm to 2400 grooves/mm. More grooves per mm increases the spectral resolution, but also decreases the optical signal throughput. Increased spectral resolution also increases the aberration that must be removed to obtain improved resolution. The choice of grating resolution depends upon the resolution required, the range covered by the CCD detector, and the degree of signal throughput desired. The volume holographic transmission grating 52 is preferably sandwiched between the two optically transparent aberration correction elements 54.

The volume holographic grating 52 is used because of its high efficiency in dispersing light into the needed spectrum and also because it can be used with very fast optical lenses. Overall signal throughput is increased by several orders of magnitude compared with conventional spectrometers using conventional reflective optics and gratings. This increased efficiency allows for enhanced sensitivity in detection of Raman signal and greater speed of detection. A currently preferred volume holographic transmission grating is commercially available from Kaiser Optical Systems, Ann Arbor, Mich. or Ralcon Labs, Paradise, Utah. The prisms, optical lenses and all optical interfaces are preferably coated with anti-reflection coatings to minimize light losses through the spectrometer.

Because the Raman spectrometer illustrated in FIG. 1 relies on fiber-optic coupling of the Raman signal to the spectrometer, the volume holographic transmission grating 52 is preferably designed for optimum efficiency with the randomly polarized light carried by the optical fiber bundle 14. The grating is preferably designed to balance the diffraction efficiency for the "s" and "p" polarization modes. This allows the grating to pass more Raman signal when confronted with a randomly polarized signal. Most holographic gratings are not designed to work efficiently in the near infrared region. Refractive index modulation in the grating is preferably optimized for near infrared operation. The emulsion thickness of the grating 52 is preferably designed thinner to obtain a flatter diffraction efficiency curve over the near infrared spectral region (840 to 950 nm).

The prisms 54 have another function in addition to correcting signal aberration caused by the volume holographic transmission grating 52. When the grating is sandwiched between two optical wedges (prisms), the grating can operate at higher effective groove densities and provide higher spectral resolution. The sandwiched prism design allows the holographic transmission grating 52 to have a grating resolution greater than 2300 grooves/mm. Normally, holographic transmission gratings operating in air alone have a practical resolution limit on the order of 1700 grooves/mm. The increase in resolution afforded by the disclosed design offers improved signal throughput for faster integration times and improved Raman signal resolution. Raman peaks that are very close together (resolution of 4.5 $cm^{-1}$) can be effectively detected and measured according to the disclosed design.

Several experiments were performed using a Raman spectroscopy apparatus as shown in FIG. 1 to analyze various petroleum products. The results of these tests are illustrated in FIGS. 6–18. The enhancement cell had a length between 0.31 and 2 meters and a diameter between 0.06 and 0.03 inches. A laser diode generating an excitation wavelength between 780 and 800 nm was used. The laser diode had a power output between 50 and 100 mW. The integration times ranged from 60 to 90 seconds.

Figure 19:
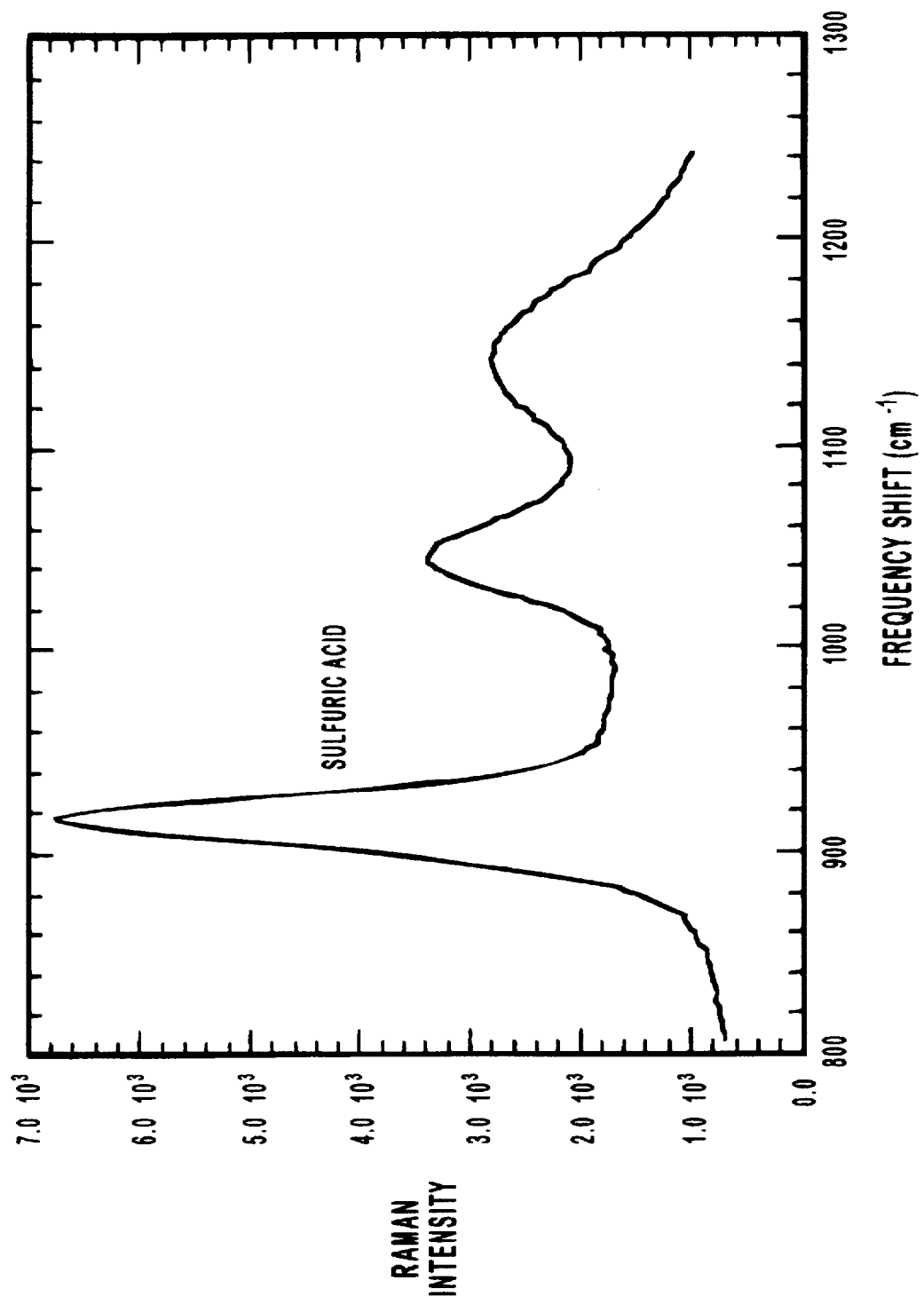
FIG. 19 is a graph of the Raman spectrum for pure sulfuric acid, with a major Raman peak at 920 cm$^{-1}$.
Figure 20:
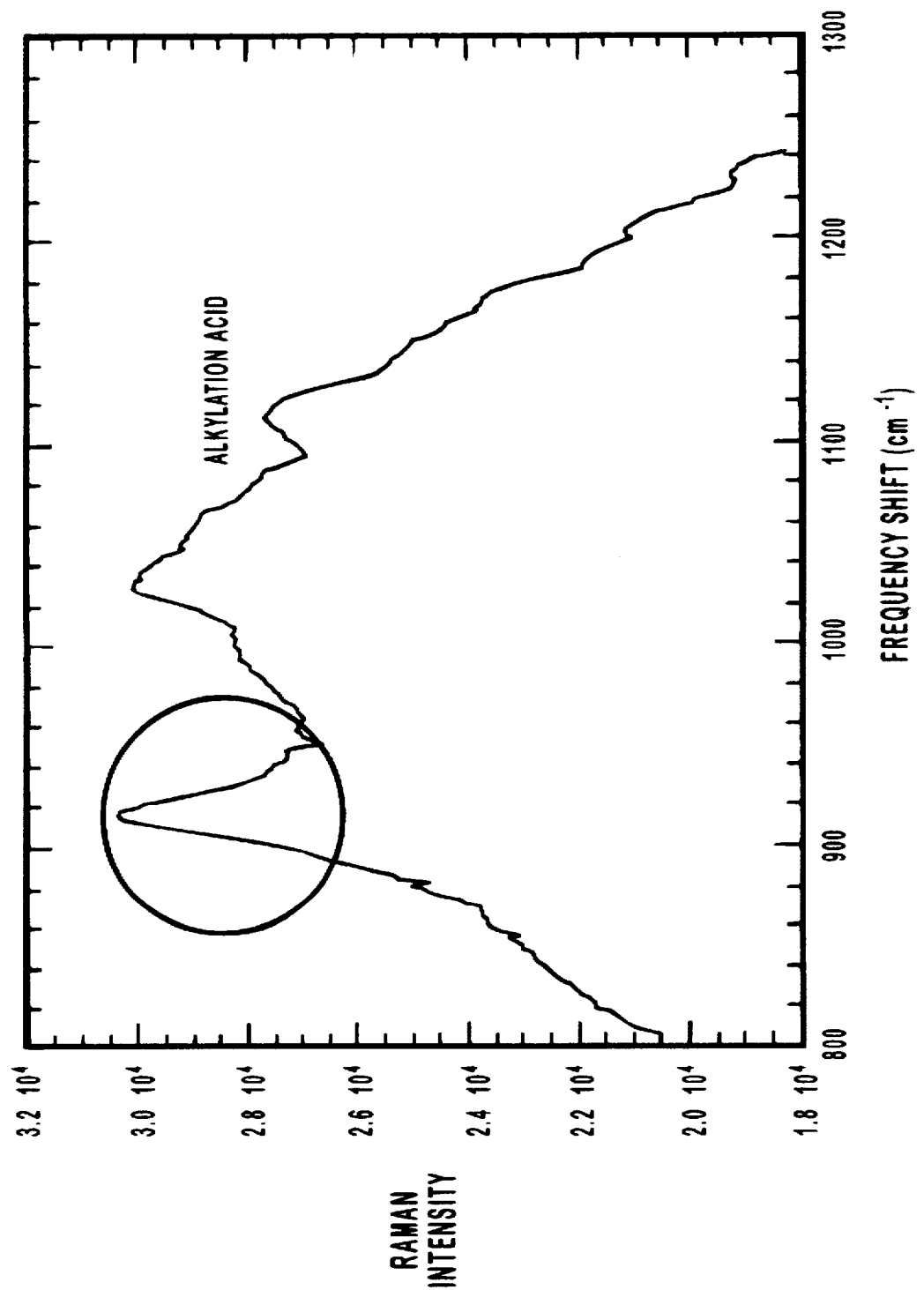
FIG. 20 is a graph of the Raman spectrum showing the sulfuric acid Raman peak present in a sample of alkylation acid.
Figure 21:
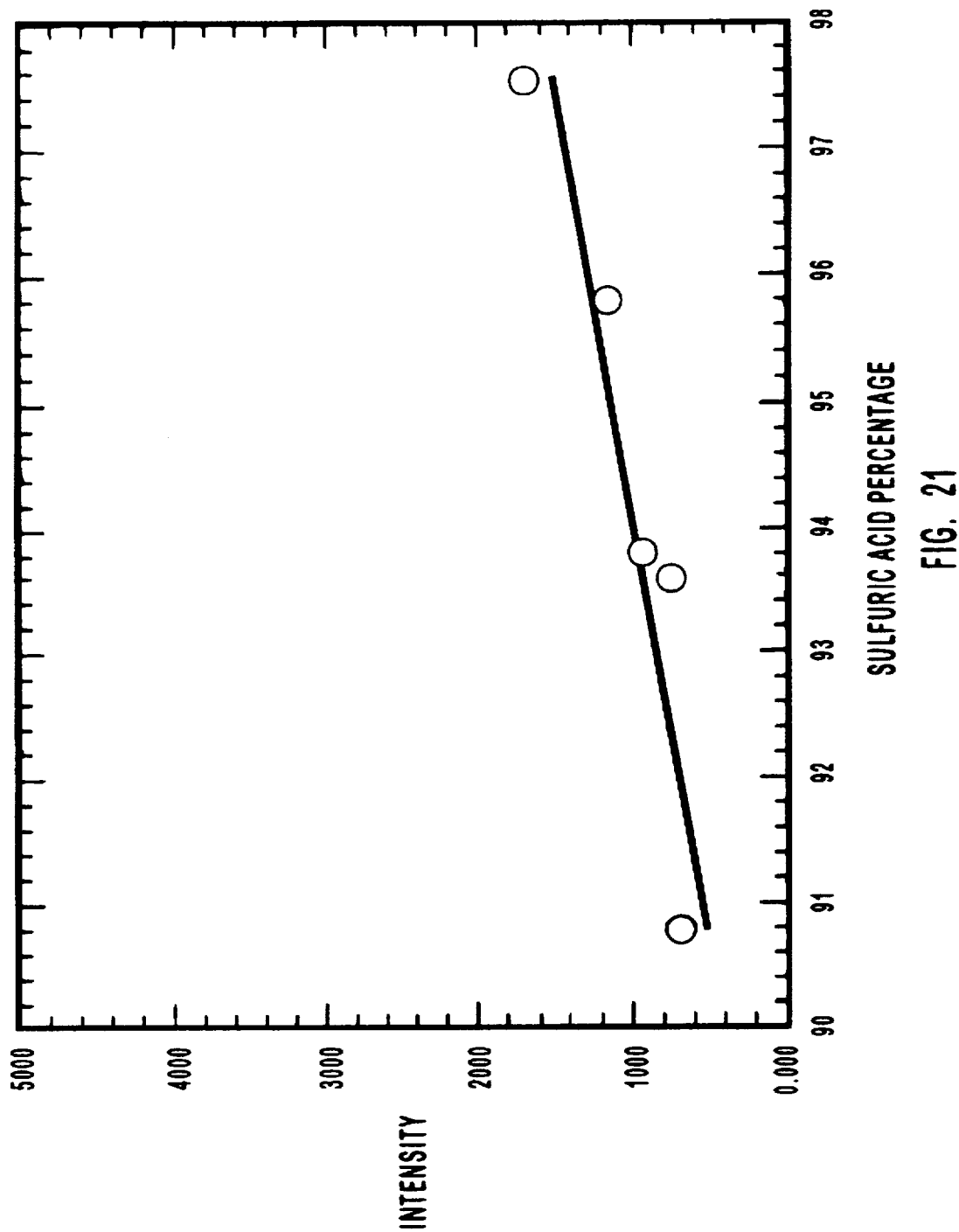
FIG. 21 is a graph of Raman intensity vs. acid percentage indicating a linear relationship between the Raman signal strength and the actual acid concentration in the alkylation acid process stream.

Additional experiments were performed to analyze sulfuric acid and process streams containing sulfuric acid. The results of these tests are illustrated in FIGS. 19–21. The Raman spectroscopy apparatus was identical to that described above, except that an excitation wavelength of 847 nm was used.

Octane determination

Figure 6:
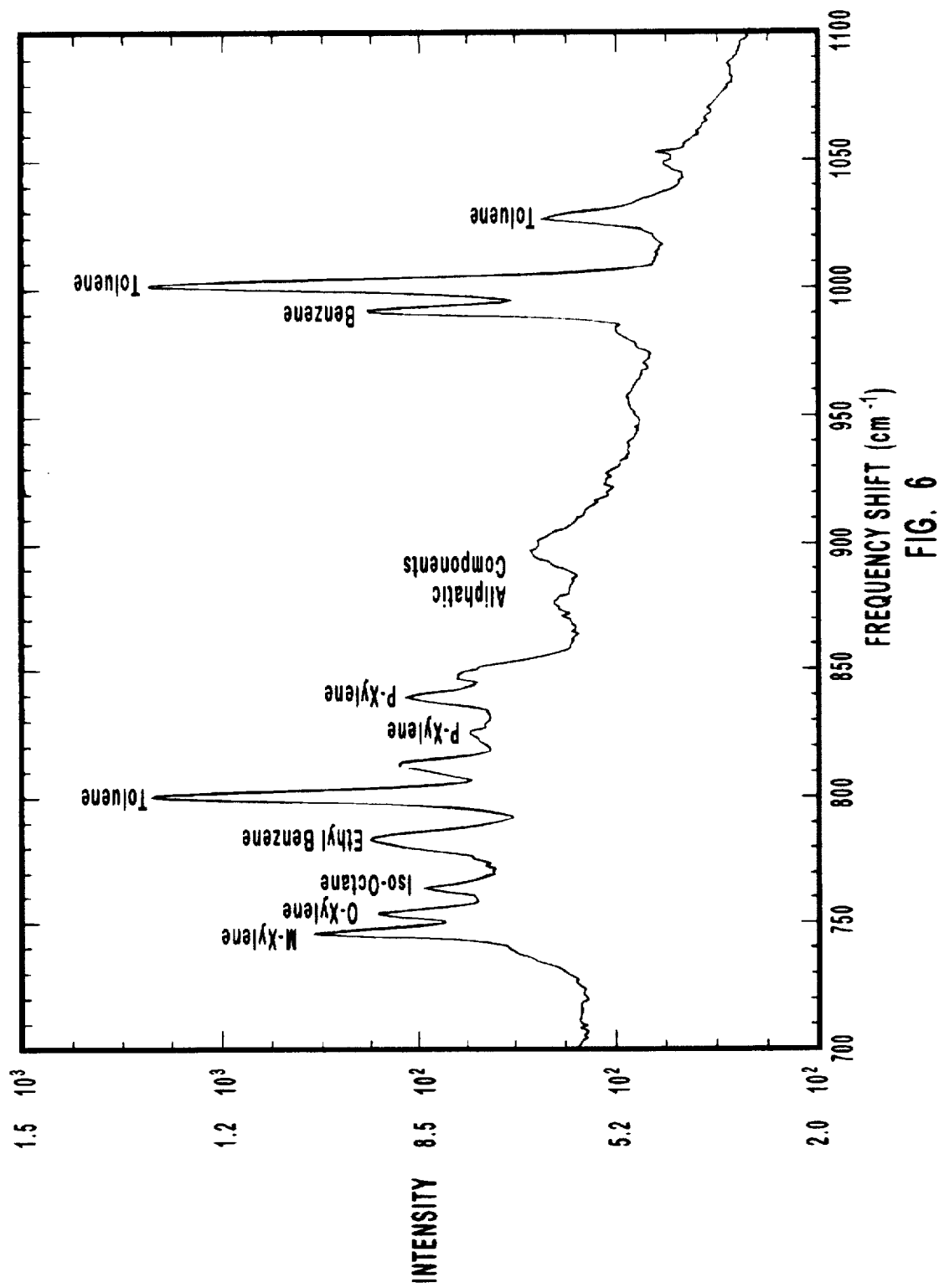
FIG. 6 is a graph of the Raman spectrum of unleaded gasoline obtained with an apparatus according to the present invention.

FIG. 6 identifies the location and relative intensities of the Raman peaks for the major constituents of gasoline. Toluene, m-, o-, and p-xylene, ethyl benzene, and benzene make up most of the important aromatic constituents. Isooctane is a major ingredient whose concentration can be adjusted to readily increase or decrease octane rating. The aliphatics, such as n-heptane and n-hexane, have Raman peaks that are much broader than the aromatics, and their peaks are illustrated in the region from 890 to 940 $cm^{-1}$. By measuring the relative intensities of the "octane enhancers" such as m-, o- and p-xylene, isooctane, ethyl benzene and toluene to the intensities of the aliphatics, one can develop a model that will determine the octane rating of the fuel. It is necessary to be able to distinguish these compounds from the aliphatics that reduce octane ratings rather than increase the octane rating. The aromatics and isooctane tend to be the most important compounds in determining octane rating and their Raman peaks are very narrow and distinct in this "finger print" region of the frequency scale, i.e., 700 to 1025 $cm^{-1}$.

Commercially available chemometric analysis software such as MATLAB, sold by The Math Works, Inc., Natick, Mass., or GRAMS/386, sold by Galactic Industries Corporation, Salem, N.H., can be used to develop the octane rating model. The combustion properties reflected in octane number can be derived from a variety of compositions of branched and aromatic hydrocarbons. Thus, the calibration model development must include a full spectrum analysis to capture the range of structures that relate to octane number. Since the composition of fuels can vary considerably, the algorithm must have robust predictive capabilities. For this task, it is currently preferred to first use the principal component regression approach of partial least squares or "PLS." This approach extracts a set of factors that capture the variation in the calibration spectra that relate to variation in the property being predicted while ignoring variation that is not related to this property. This attribute of PLS allows for a wider variation in compositions of unknowns that could be tolerated in classical least squares or more traditional principal component regression approaches.

Model development and calibration will proceed using standard samples which have been octane graded by standard knock engine techniques; samples from a variety of refineries will be brought into the calibration set. Cross-validation (leaving out the standard being tested) should be used to check the predictive capabilities of the model over the calibration set; many tests of the model and method should be performed during instrument calibration while operating on-line, in parallel with a knock engine. Continuous quality testing of the model is carried out during analysis; lack-of-fit criteria testing of the model is carried out during analysis; lack-of-fit criteria (excess spectral error, structured residuals) are examined for all unknown samples with outliers preferably stored for further evaluation. Once the model is developed and tested, suitable analysis software is developed based on the model.

Figures 7, 8:
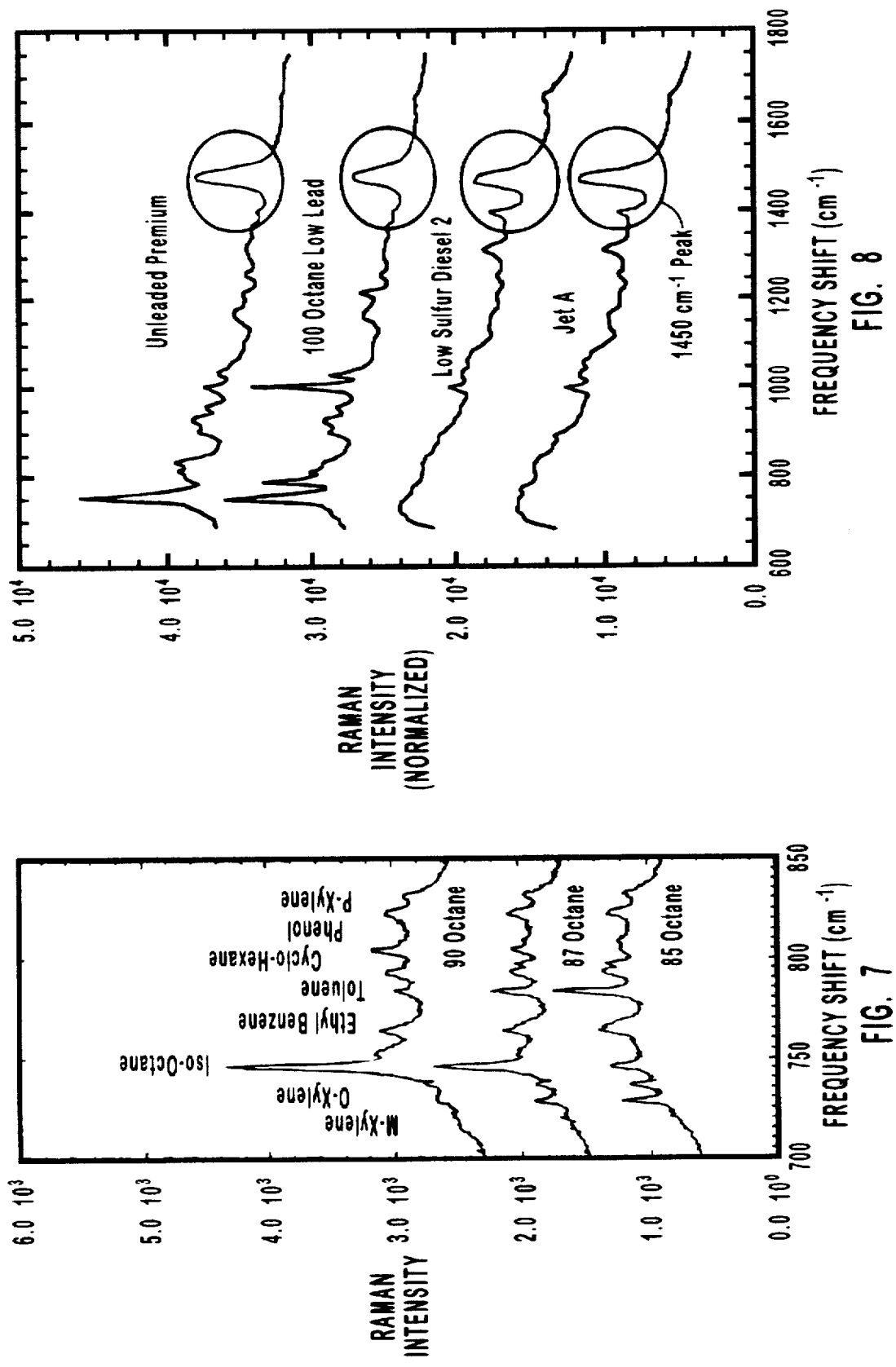
FIG. 7 is a graph of the Raman spectrum of various octane grades of gasoline fuel showing the changes in the key octane determinant peaks as the octane rating changes.
FIG. 8 is a graph of the Raman spectrum around 1400 $cm^{-1}$ and 1440 $cm^{-1}$ of different types of fuels which can be used to indicate change in the laser power.

FIG. 7 illustrates how Raman measurements can identify the changes in the key octane determinant peaks as the octane rating changes in fuel. With higher octane rating the octane enhancer isooctane increases in concentration, while toluene concentration decreases. Each petroleum company has its own special blending practices to produce their higher octane rated gasolines. The Raman spectra need to be generated for each company's gasoline and that information put into a mathematical model that can then be used to determine the octane rating for that refiner's products. A model for one company's fuel system may or may not work directly for another fuel system. The models may have to be made individually for each blending pattern.

FIG. 8 illustrates the existence of Raman peaks in the Raman spectrum around 1400 and 1440 $cm^{-1}$ that change very little with different types of fuels as well as with different octane ratings. These peaks are made up of the Raman spectra of many of the gasoline components, thus these peaks stay relatively constant with changing individual gasoline constituents. Although these peaks are not useful for analyzing a particular aliphatic or aromatic component, they can be used as an internal reference to ensure that the relative excitation energy has not changed. Because the laser diode power output can fluctuate, any changes in laser power will show up as increases or decreases in the individual Raman peaks. Examining the intensities of the Raman peaks that change very little with concentration, allows one to use this information to indicate if and when the laser power is changing. The use of these particular peaks does not mean that a routine calibration procedure is not needed; it does mean that the calibration may not have to be performed as often.

Olefin Determination

Figure 9:
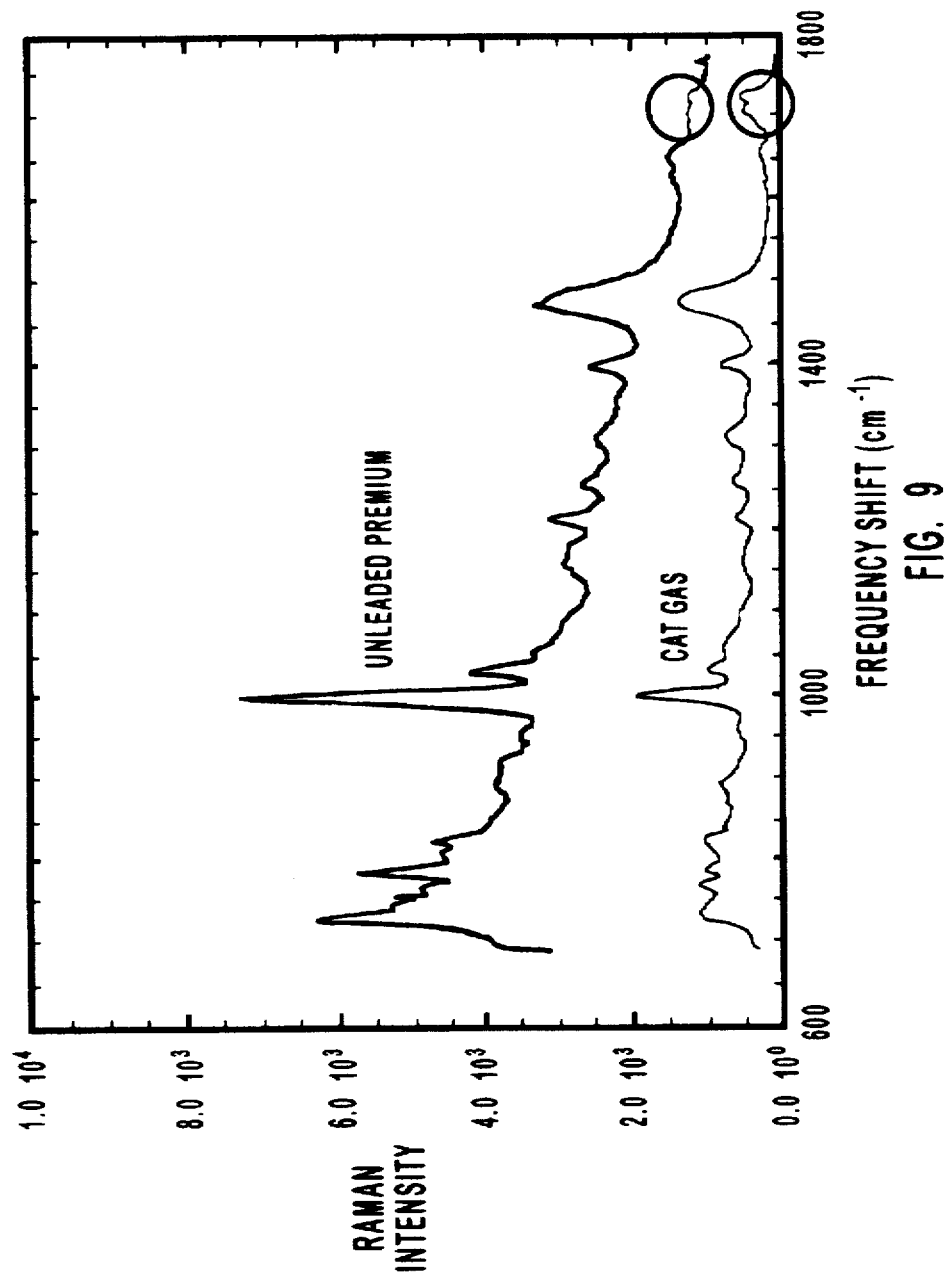
FIG. 9 is a graph of the Raman spectra of two different types of gasoline product, "cat gas" and unleaded premium (ULP), and the relative location of the olefin peaks at 1625 $cm^{-1}$ to 1725 $cm^{-1}$.

FIG. 9 illustrates the Raman spectra of two different types of gasoline product. The top curve is the Raman spectrum for a standard unleaded premium gasoline, the lower curve is for a gasoline product called "cat gas." This particular product has a very high olefin content, typically 25 to 30%. It is shown here to illustrate the relative location of the olefin peaks (encircled region) at 1625 $cm^{-1}$ to 1725 $cm^{-1}$. The unleaded gasoline has a fairly low olefin concentration, around 6.5%, so the Raman spectrum for the olefin in the unleaded gasoline is much smaller. It turns out that most of the olefins (C=C double bond) compounds have Raman peaks in the region of 1625 $cm^{-1}$ to 1725 $cm^{-1}$. There may be as many as 50 to 100 different olefin species present in gasoline. It is not necessary to measure each individual olefin component, rather the total olefin concentration as a group is sufficient. The fact that Raman spectra for most of the olefins have at least one peak in this region allows us to measure the area under this curve and determine the total olefin concentration.

Third party chemometric analysis software can be used to develop a calibration model for determining olefin concentration in a manner similar to determining octane rating described above. Once the calibration model is developed and tested, suitable analysis software is developed based on this model.

The multivariate calibration of the model would preferably utilize a maximum likelihood or classical least squares approach to estimate olefin concentrations. A two vector design matrix, confined to wavenumber regions near the olefin peak(s), would be constructed with a "pure component" olefin vector and a baseline vector. The vectors for the calibration model can be determined by least squares from a series of gasoline standards containing known olefin content, while several functional forms for the baseline are tested for quality of fit. If more than one olefin scattering band is included in the model, then each band can be individually tested for its prediction uncertainty by crossvalidation, and the results pooled and weighted by their inverse variances in the final calibration model.

The olefin concentration can be reported by application of the above model in a multivariate least squares step that determines the olefin concentration and baseline amplitude in a sample spectrum. Despite the fact that the olefin analysis requires scattering data only over a few Raman bands, the multichannel nature of the CCD-detected spectrum provides quality assurance on the validity of the model. The magnitude of the residual difference between the best fit model and the measured data would be tested for error in excess of the shot noise in the data; excess error and structure in the residuals (as assessed by an autocorrelation analysis) would indicate the presence of an interfering peak that was not present in the samples used to develop the model; if several olefin bands are used in the analysis, then alternate models could be applied where a poorly-fit band is dropped from the analysis.

Figure 10:
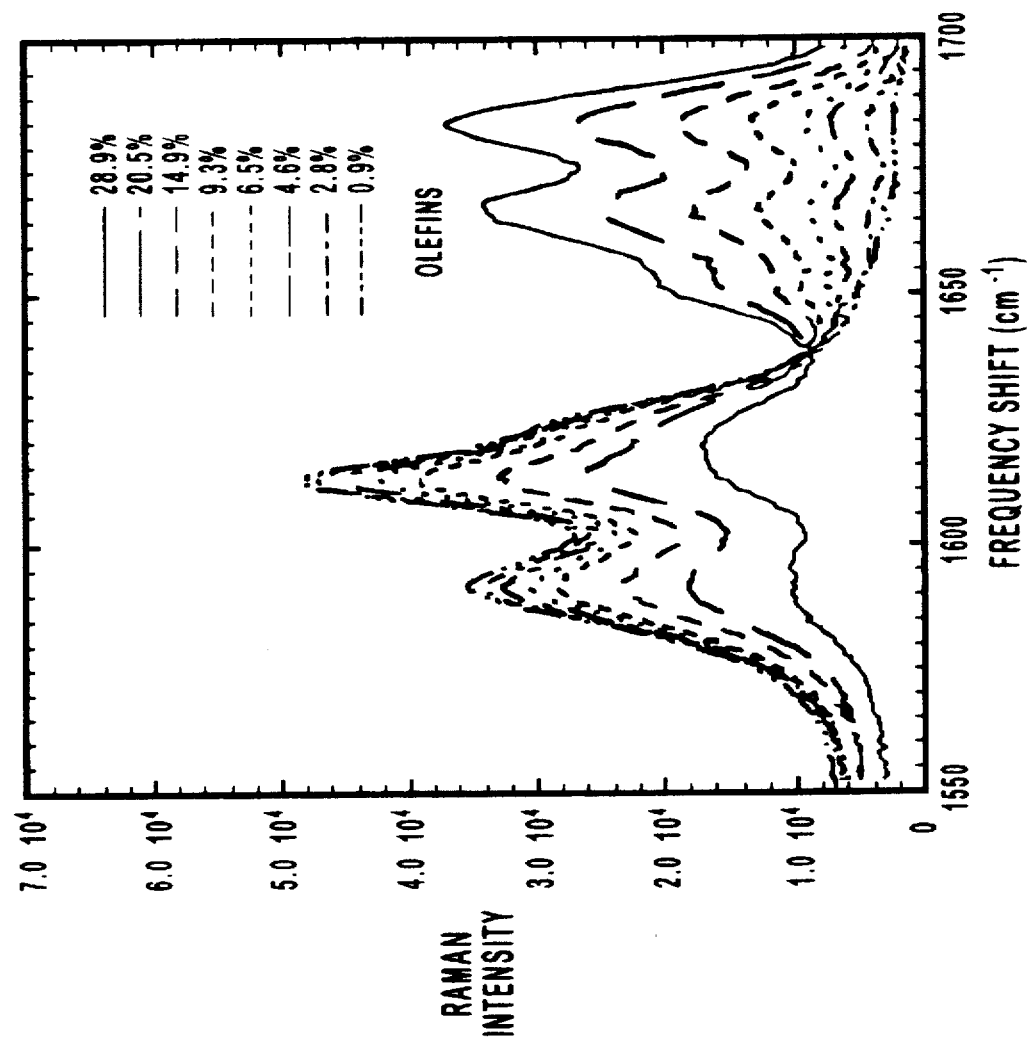
FIG. 10 is a graph of the Raman spectra of the gasolines analyzed in FIG. 9 with an expanded peak in the region from 1625 $cm^{-1}$ to 1725 $cm^{-1}$ as the olefin concentration is increased from 0.9% to almost 29%.
Figure 11:
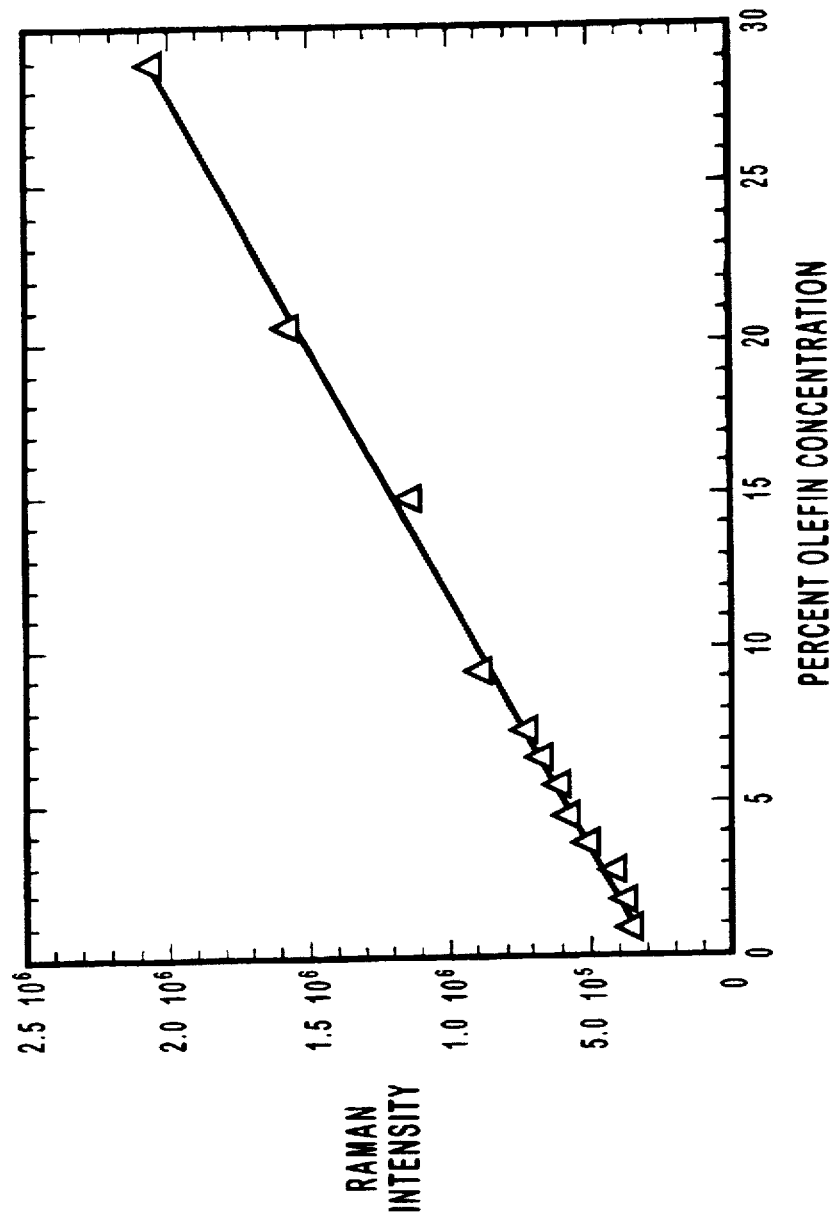
FIG. 11 is a graph of Raman intensity vs. total olefin concentration for the curves shown in FIG. 10, indicating a linear relationship between Raman signal strength and the total olefin concentration.

FIG. 10 illustrates the Raman spectra of this region (1625 to 1725 $cm^{-1}$) as the olefin concentration is increased from 0.9% to almost 29%. The areas under these curves can be plotted (see FIG. 11) and the data indicate the linear relationship between Raman signal strength and the total olefin concentration. These data can be acquired in seconds, rather than hours as with existing Florescence Indicator Analysis (F.I.A.) technology currently being used in refineries.

Xylene Determination

The three isomers of xylene, meta, ortho, and para, are very valuable as starting materials for petrochemicals. For this reason, they are often removed from gasoline and sold to chemical processing plants. The concentrations of the three individual xylene isomers are difficult to measure quickly and to separate from other contaminating aromatics, such as benzene, toluene, and ethyl benzene. Xylenes are used in such large volume that their rapid and accurate measurement is essential. Current chromatography techniques require nearly fifteen to twenty minutes to analyze for the relative concentrations of the individual isomers. In large chemical processing plants this analysis is just too slow.

Figure 12:
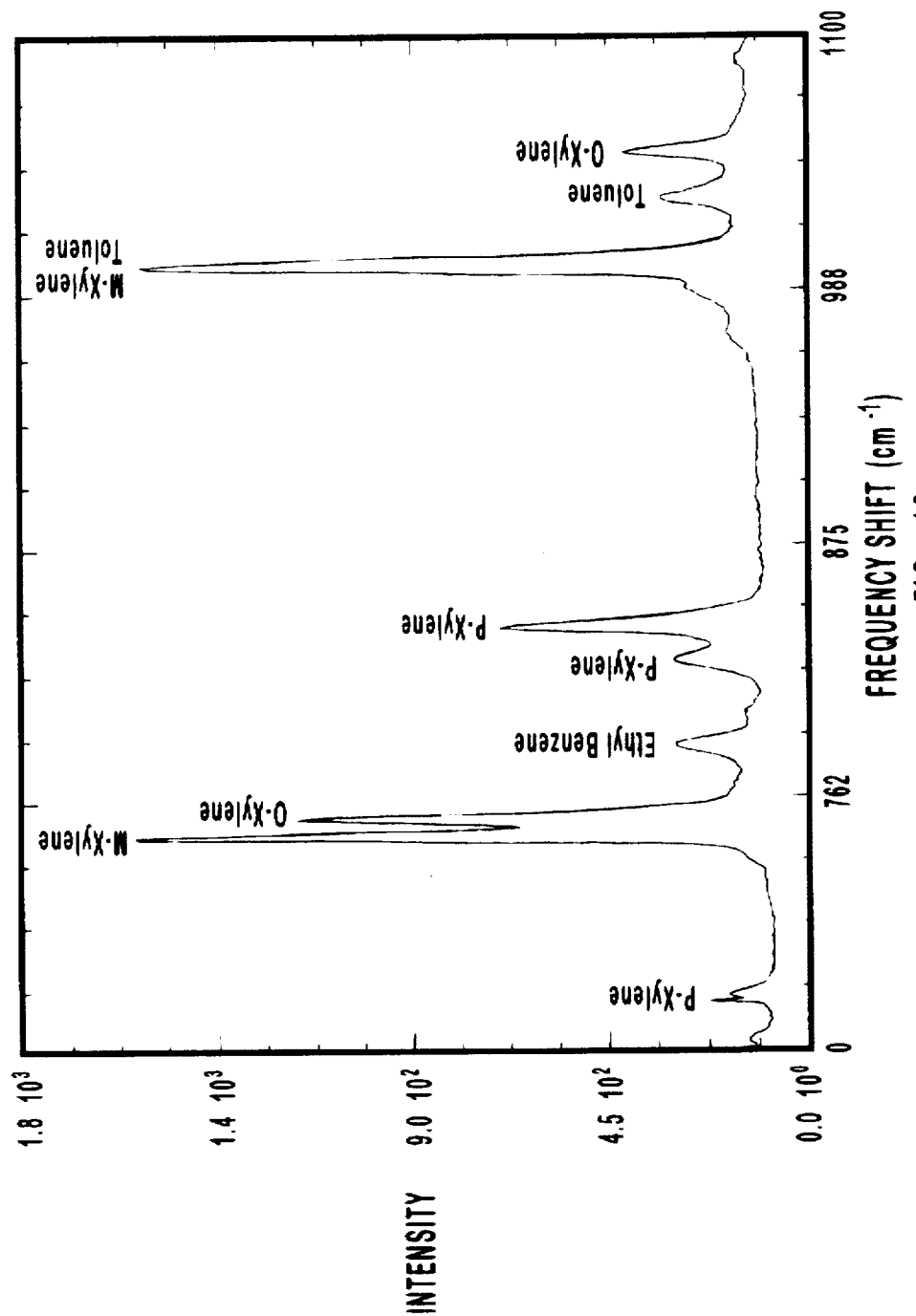
FIG. 12 is a graph of the Raman spectrum of a predistillate fraction rich in xylene illustrating the individual Raman peaks for the various xylene isomers, m-, o-, and p-xylene.

FIG. 12 illustrates the individual Raman peaks for the various xylene isomers, m-, o-, and p-xylene in a predistillate fraction rich in xylene. These components can easily be differentiated from the other commonly occurring aromatics, such as ethyl-benzene, toluene and benzene.

Benzene Concentration Determination

Because benzene is considered a carcinogen, problems surrounding locating its extent, concentration, and safe containment or removal are of utmost concern. EPA Clean Air rules currently in effect require petroleum refiners to reduce benzene levels in gasoline to below 1%. Traditional process chromatography is normally too slow, requiring 15 to 20 minutes per test. Infrared absorption (IR) requires too short of a cell path length, and Near-IR is not sensitive enough. Recent EPA regulations will force a broad range of industries to cut emissions of benzene that pose cancer risks to workers frequently in contact with petroleum products.

Figure 13:
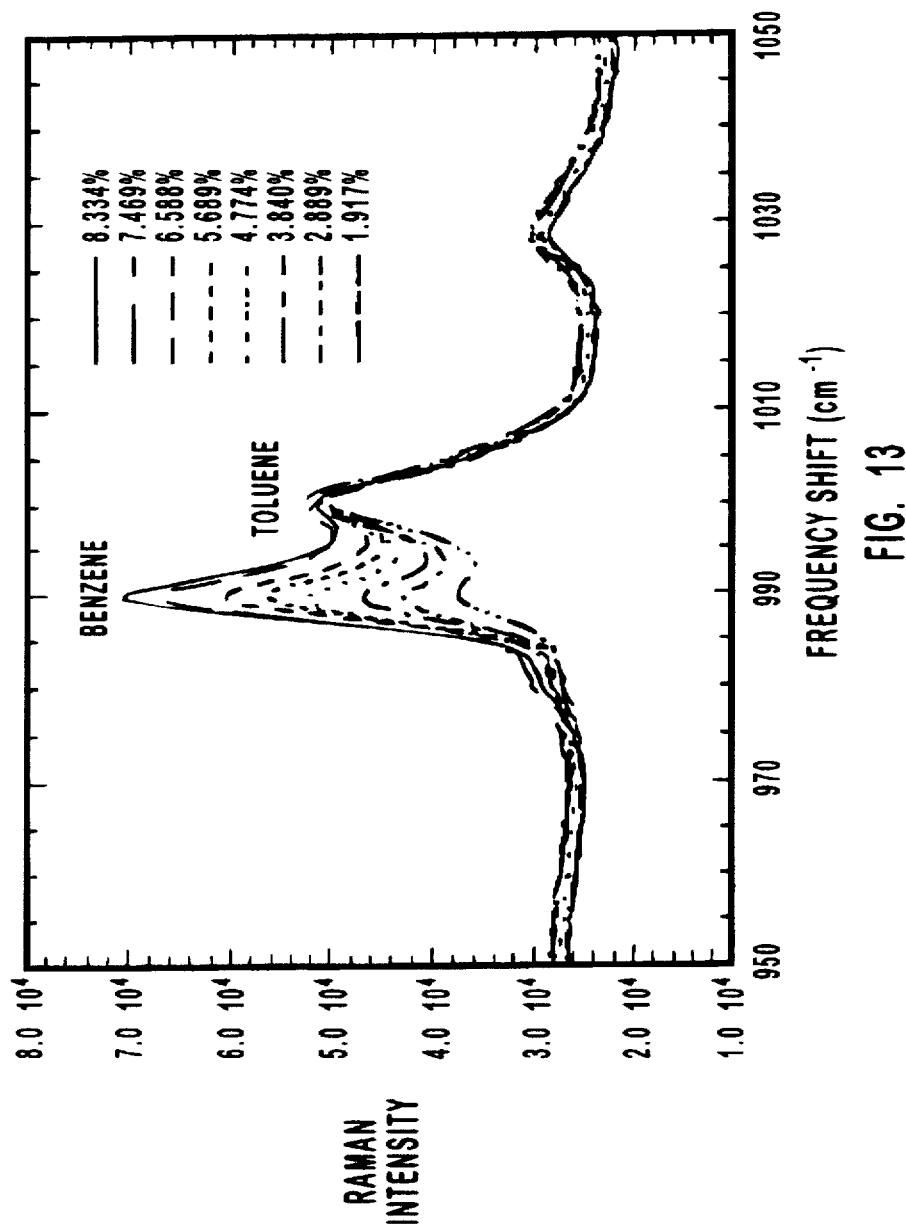
FIG. 13 is a graph of the Raman spectra for increasing concentrations of benzene in unleaded premium gasoline.
Figure 14:
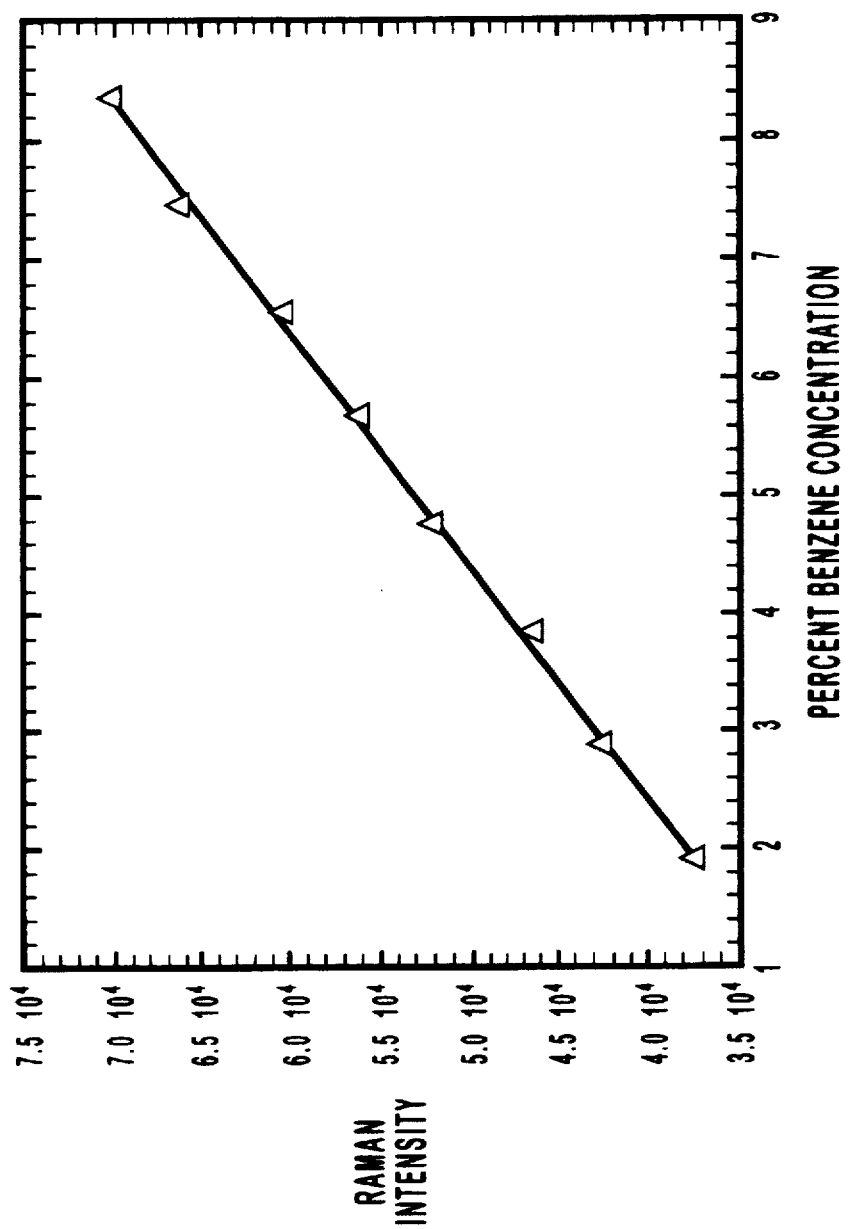
FIG. 14 is a graph of Raman intensity vs. the benzene concentration for the curves shown in FIG. 13, indicating a linear relationship between Raman signal strength and the benzene concentration in the gasoline sample.

FIG. 13 illustrates the Raman spectra for increasing concentrations of benzene in unleaded premium gasoline. FIG. 14 illustrates the linear relationship between the area under the Raman benzene peak and the benzene concentration in the gasoline sample.

Fuel Differentiation Application

Figure 15:
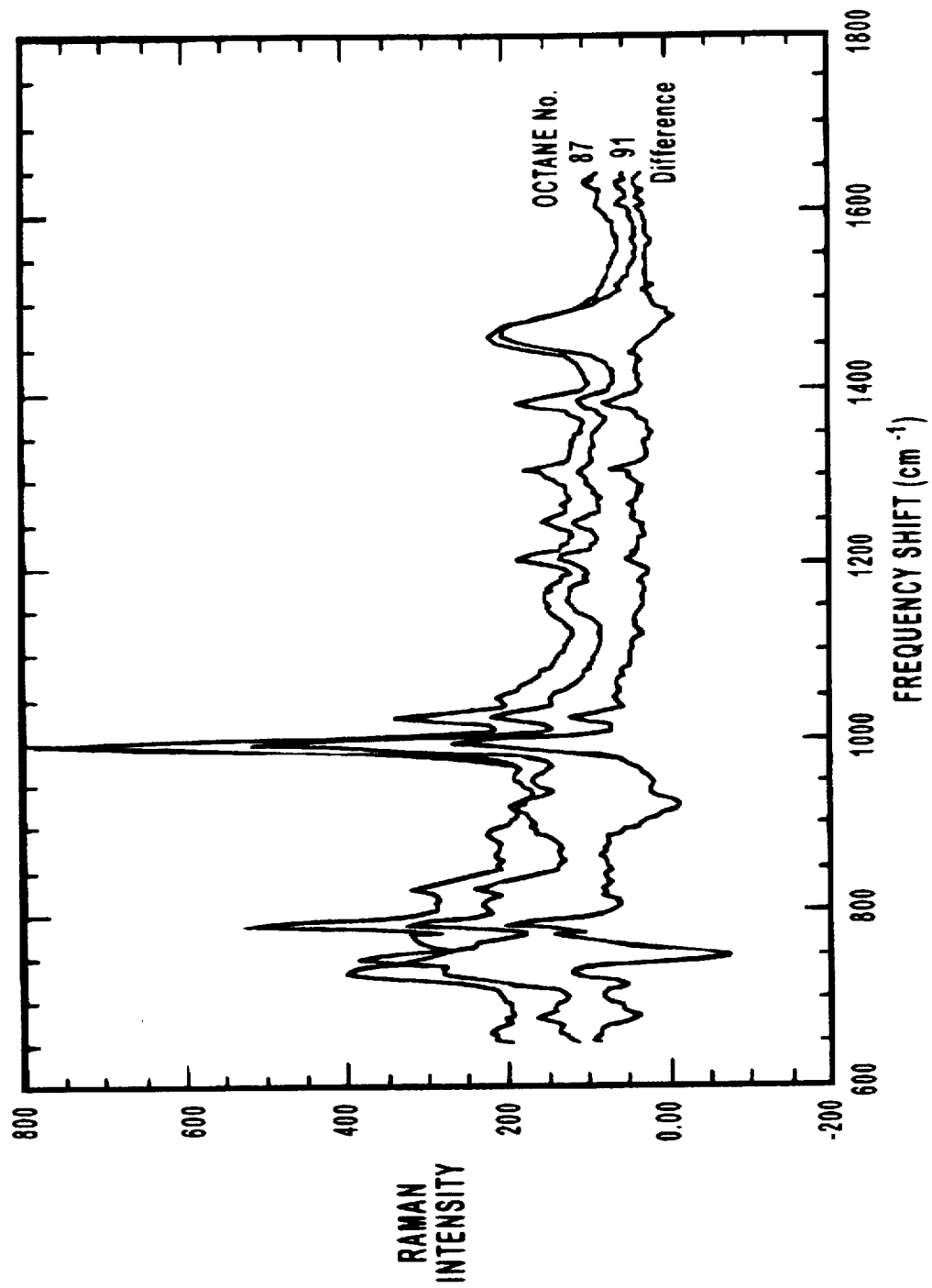
FIG. 15 is a graph of the Raman spectra for two different octane rated gasolines and the subtracted Raman spectrum of the two Raman spectra.

FIG. 15 illustrates the subtraction of two different octane rated gasolines. Since the Raman spectra are different for different fuel formulations, their difference spectra can be used to verify or substantiate that indeed two fuel systems are the same or different from one another. It is not easy for petroleum manufacturers to readily determine if a fuel sample was manufactured by them or their competitor. The ability to compare complete Raman spectra make it relatively easy to test two different fuels and determine how similar they are to one another.

Figure 16:
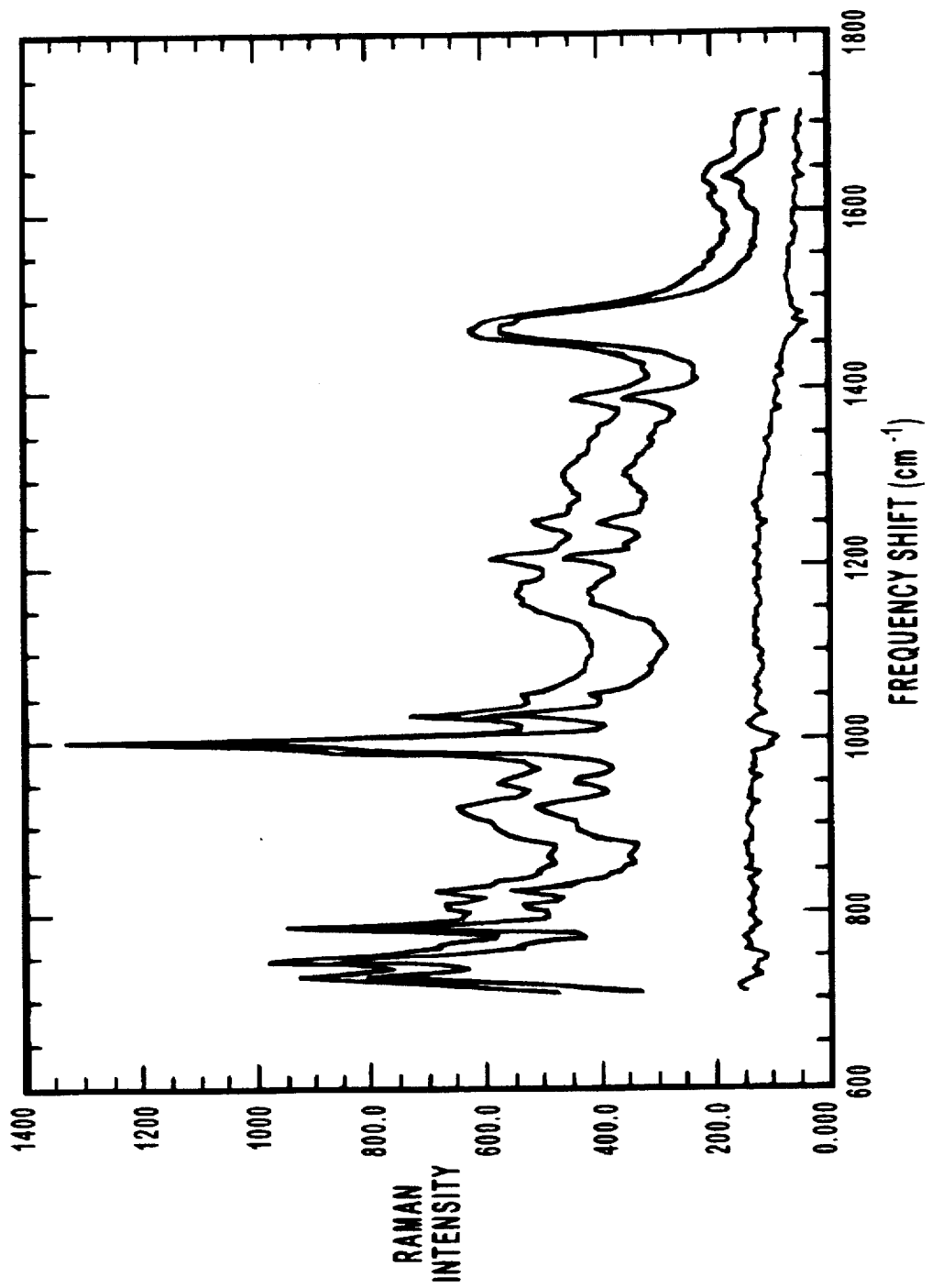
FIG. 16 is a graph of the Raman spectra for two fuel samples from the same manufacturer having the same octane rating and the subtracted Raman spectrum of the two Raman spectra.

FIG. 16 illustrates this same subtraction process applied to two samples of fuel that are in fact the same. The subtracted spectrum is basically a flat line. This type of analysis can be used in pipelines to rapidly determine when one company's fuel has stopped flowing and another company's fuel has begun, or when one fuel type has been replaced by another. In large transmission lines, many different fuel types and brands are carried together, one right after another. Density measurements are often used to determine when one particular fuel is different from another. The density of diesel is sufficiently different from gasoline that this particular test can be used. However, the density does not change sufficiently between two different brand of gasoline to readily determine the cutoff point. The analysis of cutoff point in a pipe line could easily be determined by Raman analysis according to the present invention.

Figure 17:
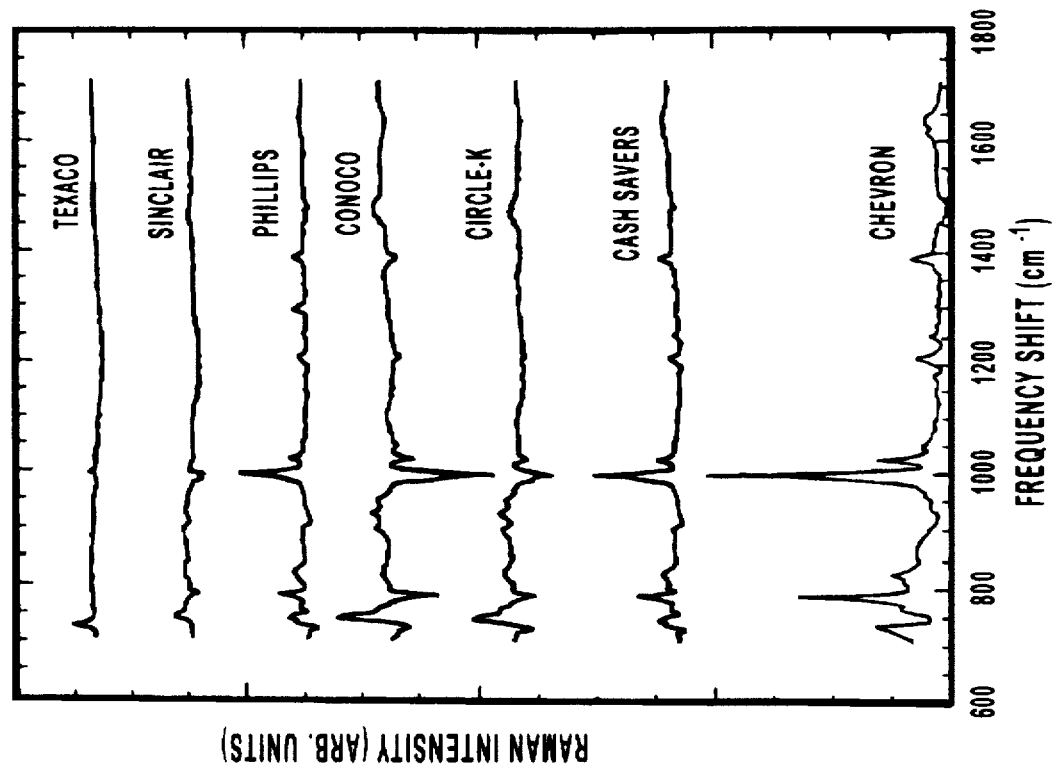
FIG. 17 is a graph of the subtracted Raman spectra for various brands of gasoline subtracted from a single brand of gasoline.

FIG. 17 illustrates the comparison of the subtracted Raman spectra for various brands of gasoline subtracted from a single brand, in this case an Amoco sample. For most of the samples, it was easy to determine that the samples were different, that a Conoco gasoline was different from the Amoco gasoline, etc. Two of the fuels tested have straight lines, indicating that they are identical to the Amoco fuel. It was verified that the Texaco and Sinclair fuel samples tested were made by Amoco. Those two refiners purchased their fuel from a local Amoco refinery rather than transporting their fuel from distant facilities.

Figure 18:
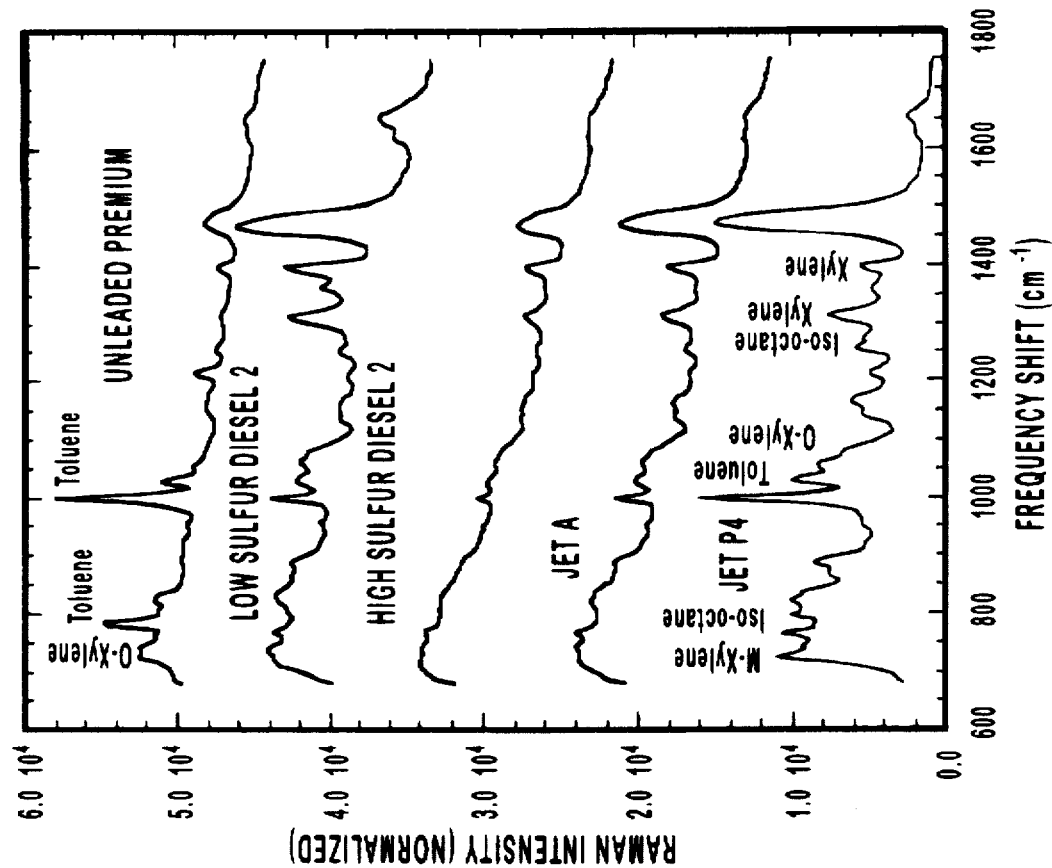
FIG. 18 is a graph of the Raman spectra for different types of fuels indicating the ability to identify the type of fuel from its unique Raman spectrum.

FIG. 18 illustrates the Raman spectra for different types of fuel systems, high and low sulfur diesel, Jet A, Jet JP4, and unleaded premium gasoline. It is apparent that their Raman spectra are unique and can be used to identify the type of fuel.

Alkylation Acid Concentration Determination

FIG. 19 illustrates the Raman spectra for pure sulfuric acid, with a major Raman peak at 920 $cm^{-1}$. FIG. 20 illustrates this same sulfuric acid Raman peak present in a sample of alkylation acid. The Raman spectra for this and other sulfuric acid Raman peaks can be used to determine the actual acid concentration in the alkylation acid process. The acid content is currently determined by conventional titration techniques. The area under the sulfuric acid Raman peaks has a linear relationship to actual acid concentration in the alkylation acid process as illustrated in FIG. 21.

It should be appreciated that the apparatus and method for analyzing the composition of a fluid stream according to the present invention are capable of being incorporated in the form of a variety of embodiments, only a few of which have been illustrated and described above. The invention may be embodied in other forms without departing from its essential characteristics. The described embodiments are to be considered in all respects only as illustrative and not restrictive and the scope of the invention is, therefore, indicated by the appended claims rather than by the foregoing description.

What is claimed is:

1. A method for continuously analyzing the composition of a fluid stream using Raman spectroscopy comprising the steps of:
   (a) introducing the fluid stream into a tubular Raman enhancement cell comprising:
      a fluid stream inlet and a fluid stream outlet located adjacent the ends of the enhancement cell for continuous fluid flow through the enhancement cell;
      an optical connector located at one end of the enhancement cell for connecting a bundle of optical fibers to the enhancement cell, wherein said bundle of optical fibers includes at least one excitation optical fiber and one or more collection optical fibers; and
      a transparent fluid barrier located between the bundle of optical fibers and the enhancement cell;
   (b) introducing light having an excitation wavelength into the Raman enhancement cell through the excitation optical fiber;
   (c) collecting backscattered Raman light from the enhancement cell with the one or more collection optical fibers;
   (d) measuring the backscattered light with a Raman spectrometer comprising:
      a linear array of the one or more collection optical fibers for generating an optical signal of the scattered light from the enhancement cell;
      a filter for rejecting portions of the optical signal having the excitation wavelength;
      a volume holographic transmission grating to disperse the light;
      a transmissive aberration correction element for correcting optical aberrations introduced into optical signal by the volume holographic transmission grating, said aberration correction element comprising at least one optically transparent wedge or prism; and
      a charge coupled device array for converting the optical signal into a corresponding electronic signal; and
   (e) converting the electronic signal into a representation of the chemical analysis of the fluid stream.

2. A method as defined in claim 1, wherein the backscattered light is measured with a Raman spectrometer comprising a plurality of optical lenses for receiving and conveying the optical signal from the linear array of the collection optical fibers to the charge coupled device array.

3. A method as defined in claim 1, wherein the fluid stream introduced into a tubular Raman enhancement cell contains petroleum products.

4. A method as defined in claim 1, further comprising the step of positioning the Raman enhancement cell at a remote location from the Raman spectrometer.

5. A method as defined in claim 1, wherein the tubular Raman enhancement cell is lined with a material having an index of refraction less than the index of refraction of the fluid stream.

6. A method as defined in claim 5, wherein the tubular Raman enhancement cell is lined with a fluorinated polymer.

7. A method as defined in claim 6, wherein the fluorinated polymer is selected from the group consisting of polytetrafluoroethylene (PTFE), FEP, PFA, AF and Tefzel.

8. A method as defined in claim 5, wherein the fluid stream introduced into a tubular Raman enhancement cell contains petroleum products and wherein the tubular Raman enhancement cell is lined with a polymer having an index of refraction less than 1.4.

9. A method as defined in claim 5, wherein the fluid stream introduced into a tubular Raman enhancement cell contains aqueous or biological solutions and wherein the tubular Raman enhancement cell is lined with a polymer having an index of refraction less than 1.33.

10. A method as defined in claim 1, wherein the tubular Raman enhancement cell has a length in the range from about 0.1 m to about 4 m.

11. A method as defined in claim 1, wherein the tubular Raman enhancement cell has a diameter in the range from about 0.005 to 0.2 inches.

12. A method as defined in claim 1, further comprising the step of aligning the tubular Raman enhancement cell in a linear orientation between the fluid stream inlet and the fluid stream outlet.

13. A method as defined in claim 1, further comprising the step of aligning the tubular Raman enhancement cell in a curved orientation between the fluid stream inlet and the fluid stream outlet.

14. A method as defined in claim 1, wherein the aberration correction element comprises two optically transparent wedges or prisms.

15. A method as defined in claim 1, wherein the bundle of optical fibers includes from 20 to 50 collection optical fibers.

16. A method as defined in claim 1, wherein the backscattered light is measured with a Raman spectrometer comprising an optical slit.

17. A method as defined in claim 16, wherein the optical slit has dimensions comparable to the linear array of collection optical fibers.

18. A method as defined in claim 16, wherein the optical slit has a width in the range from 10 microns to 150 microns.

19. A method as defined in claim 1, wherein the transparent fluid barrier includes a layer of index matching fluid to maintain optimum optical coupling between the bundle of optical fibers and the fluid barrier.

20. An apparatus for analyzing the composition of a fluid stream using Raman spectroscopy comprising:
   a laser source for producing light having an excitation wavelength;
   a bundle of optical fibers comprising one or more excitation optical fibers and a plurality of collection optical fibers;
   a tubular Raman enhancement cell comprising:
      a fluid stream inlet and a fluid stream outlet located adjacent the ends of the enhancement cell for continuous fluid flow through the enhancement cell;
      an optical connector located at one end of the enhancement cell for connecting the bundle of optical fibers to the enhancement cell; and
      a transparent fluid barrier located between the bundle of optical fibers and the enhancement cell;
   a Raman spectrometer comprising:
      a linear array of the collection optical fibers for generating a linear optical signal of the scattered light from the enhancement cell;
      a filter for rejecting portions of the optical signal having the excitation wavelength;
      a volume holographic transmission grating to disperse the signal and a transmissive aberration correction element for correcting optical aberrations introduced into optical signal by the volume holographic transmission grating, said aberration correction element comprising at least one optically transparent wedge or prism; and
      a charge coupled device array for converting the optical signal into a corresponding electronic signal; and a computer for converting the electronic signal into a representation of the chemical analysis of the fluid stream.

21. An apparatus as defined in claim 20, wherein the Raman spectrometer further comprises a plurality of optical lenses for receiving and conveying the optical signal from the linear array of the collection optical fibers to the charge coupled device array.

22. An apparatus as defined in claim 20, wherein the tubular Raman enhancement cell is lined with a material having an index of refraction less than the index of refraction of the fluid stream.

23. An apparatus as defined in claim 20, wherein the tubular Raman enhancement cell is lined with a fluorinated polymer.

24. An apparatus as defined in claim 23, wherein the fluorinated polymer is selected from the group consisting of polytetrafluoroethylene (PTFE), FEP, PFA, AF and Tefzel.

25. An apparatus as defined in claim 20, wherein the fluid stream contains petroleum products and the tubular Raman enhancement cell is lined with a polymer having an index of refraction less than 1.4.

26. An apparatus as defined in claim 20, wherein the fluid stream contains aqueous or biological solutions and the tubular Raman enhancement cell is lined with a polymer having an index of refraction less than 1.33.

27. An apparatus as defined in claim 20, wherein the tubular Raman enhancement cell has a length in the range from about 0.1 m to about 4 m.

28. An apparatus as defined in claim 20, wherein the tubular Raman enhancement cell has a diameter in the range from about 0.005 to 0.2 inches.

29. An apparatus as defined in claim 20, wherein the tubular Raman enhancement cell is constructed of a flexible material.

30. An apparatus as defined in claim 20, wherein the tubular Raman enhancement cell is constructed of a rigid material.

31. An apparatus as defined in claim 20, wherein the aberration correction element comprises two optically transparent wedges or prisms.

32. An apparatus as defined in claim 31, wherein the volume holographic transmission grating is in physical contact with the aberration correction element.

33. An apparatus as defined in claim 20, wherein the aberration correction element and optical lenses are coated with anti-reflection coatings to minimize light losses.

34. An apparatus as defined in claim 20, wherein the bundle of optical fibers includes from 20 to 50 collection optical fibers.

35. An apparatus as defined in claim 20, wherein the Raman spectrometer further comprises an optical slit.

36. An apparatus as defined in claim 35, wherein the optical slit has dimensions comparable to the linear array of collection optical fibers.

37. An apparatus as defined in claim 35, wherein the optical slit has a width in the range from 10 microns to 150 microns.

38. An apparatus as defined in claim 20, wherein the transparent fluid barrier includes a lens.

39. An apparatus as defined in claim 20, wherein the transparent fluid barrier includes an optical window.

40. An apparatus as defined in claim 20, wherein the transparent fluid barrier includes a layer of index matching fluid to maintain optimum optical coupling between the bundle of optical fibers and the fluid barrier.

41. An apparatus for analyzing the composition of a sample using Raman spectroscopy comprising:

a laser source for producing light having an excitation wavelength, wherein the light is directed into a sample and wherein a Raman signal exits the sample as an optical signal;

a Raman spectrometer configured to receive the optical signal comprising:

a filter for rejecting portions of the optical signal having the excitation wavelength;

an optical slit;

a volume holographic transmission grating to disperse the optical signal and a transmissive aberration correction element for correcting optical aberrations introduced into optical signal by the volume holographic transmission grating, said aberration correction element comprising at least one optically transparent wedge or prism; and a charge coupled device array for converting the optical signal into a corresponding electronic signal; and a computer for converting the electronic signal into a representation of the chemical analysis of the sample.

42. An apparatus as defined in claim 41, wherein the Raman spectrometer further comprises a plurality of optical lenses for receiving and conveying the optical signal to the charge coupled device array.

43. An apparatus as defined in claim 41, wherein the aberration correction element comprises two optically transparent wedges or prisms.

44. An apparatus as defined in claim 43, wherein the volume holographic transmission grating is in physical contact with the aberration correction element.

45. An apparatus as defined in claim 41, wherein the aberration correction element and optical lenses are coated with anti-reflection coatings to minimize light losses.

* * * * *